United States Patent
Tanabe et al.

(10) Patent No.: US 9,862,993 B2
(45) Date of Patent: Jan. 9, 2018

(54) GENETIC ANALYSIS SYSTEM

(71) Applicant: HITACHI, LTD., Tokyo (JP)

(72) Inventors: Maiko Tanabe, Tokyo (JP); Hideki Kambara, Tokyo (JP); Masataka Shirai, Tokyo (JP)

(73) Assignee: HITACHI, LTD., Tokyo (JP)

( * ) Notice: Subject to any disclaimer, the term of this patent is extended or adjusted under 35 U.S.C. 154(b) by 25 days.

(21) Appl. No.: 15/028,907

(22) PCT Filed: Oct. 21, 2013

(86) PCT No.: PCT/JP2013/078426
§ 371 (c)(1),
(2) Date: Apr. 12, 2016

(87) PCT Pub. No.: WO2015/059741
PCT Pub. Date: Apr. 30, 2015

(65) Prior Publication Data
US 2016/0251705 A1 Sep. 1, 2016

(51) Int. Cl.
*C12Q 1/68* (2006.01)
*B01L 3/00* (2006.01)

(52) U.S. Cl.
CPC .......... *C12Q 1/6837* (2013.01); *B01L 3/5085* (2013.01); *C12Q 1/6809* (2013.01);
(Continued)

(58) Field of Classification Search
CPC .......... C12Q 1/68; C07H 21/04; C40B 30/04; G01N 31/22
See application file for complete search history.

(56) References Cited

U.S. PATENT DOCUMENTS

| 6,232,067 B1 * | 5/2001 | Hunkapiller | C12Q 1/6809 435/5 |
| 6,677,121 B2 * | 1/2004 | Lizardi | C12Q 1/6809 435/6.1 |
| 8,486,628 B2 * | 7/2013 | Loeffert | C12Q 1/6851 435/6.1 |

FOREIGN PATENT DOCUMENTS

| JP | 2006-029953 A | 2/2006 |
| JP | 2006-520206 A | 9/2006 |

(Continued)

OTHER PUBLICATIONS

Goetz et al., "Transcriptome sequencing of single cells with Smart-Seq," *Nature Biotechnology*, vol. 30, No. 8, pp. 763-765 (2012).
(Continued)

*Primary Examiner* — Narayan Bhat
(74) *Attorney, Agent, or Firm* — Baker Botts L.L.P.

(57) ABSTRACT

In order to decode arbitrary sequence regions for a large number of genes in a large number of cells, it is necessary to fragment the nucleic acids and introduced a sequence, which differs for each the cell, in the respective fragments. However, in conventional constructions for analyzing large numbers of cells, there was the problem that the cleaved fragments of different regions were intermingled before a tag sequence unique to each region could be introduced. The present invention is constructed to also comprise a genetic analysis system, when trapping nucleic acids extracted from a cell in multiple regions on a substrate and synthesizing and fragmenting the complementary DNA strands (cDNA) of the nucleic acids for each individual region, for immediately introducing a tag sequence unique to each of the regions into said fragments.

15 Claims, 15 Drawing Sheets

(52) U.S. Cl.
CPC .......... *B01L 2300/0819* (2013.01); *B01L 2300/0893* (2013.01)

(56) References Cited

FOREIGN PATENT DOCUMENTS

| | | |
|---|---|---|
| JP | 2007-319028 A | 12/2007 |
| JP | 2009-276883 A | 11/2009 |
| JP | 2010-022384 A | 2/2010 |
| WO | WO2006/117541 * | 11/2006 |
| WO | WO 2011/068088 A1 | 6/2011 |
| WO | WO 2013/145431 A1 | 10/2013 |

OTHER PUBLICATIONS

Hashimshony et al., "CEL-Seq: Single-Cell RNA-Seq by Multiplexed Linear Amplification," *Cell Reports*, vol. 2, pp. 666-673 (2012).

Taniguchi et al., "Quantitative analysis of gene expression in a single cell by qPCR," *Nature Methods*, 7 pages (2009).

International Search Report, dated Jan. 21, 2014, which issued during the prosecution of International Patent Application No. PCT/JP2013/078426, which corresponds to the present application.

\* cited by examiner

Fig. 1
(a)
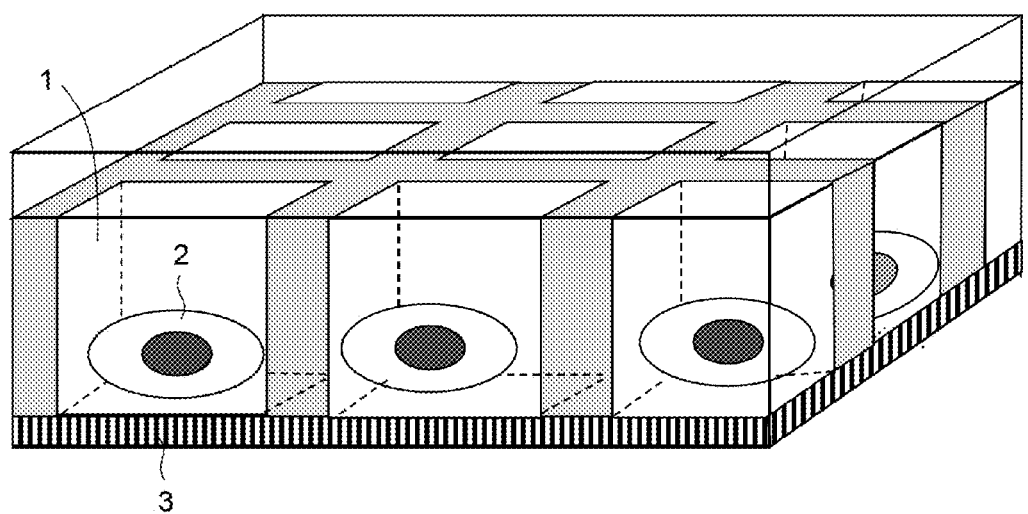
(b)
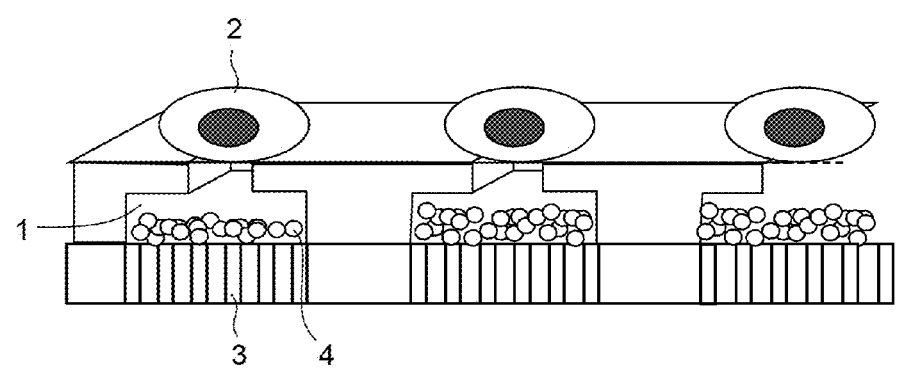

Fig. 5
(a)
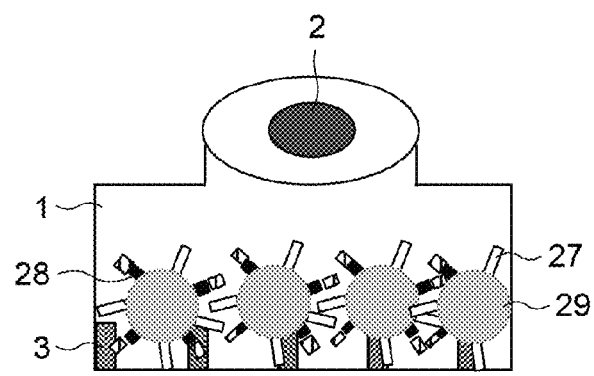
(b)
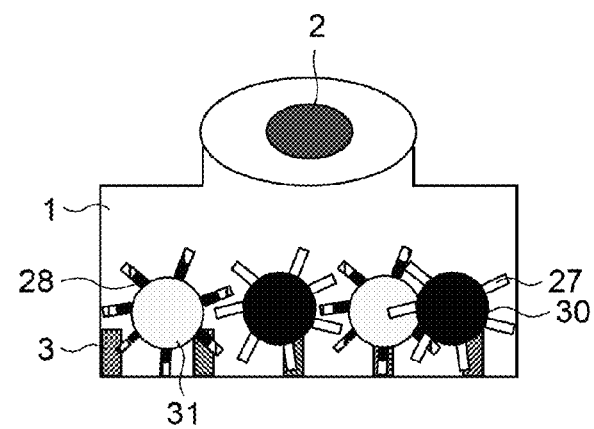
(c)
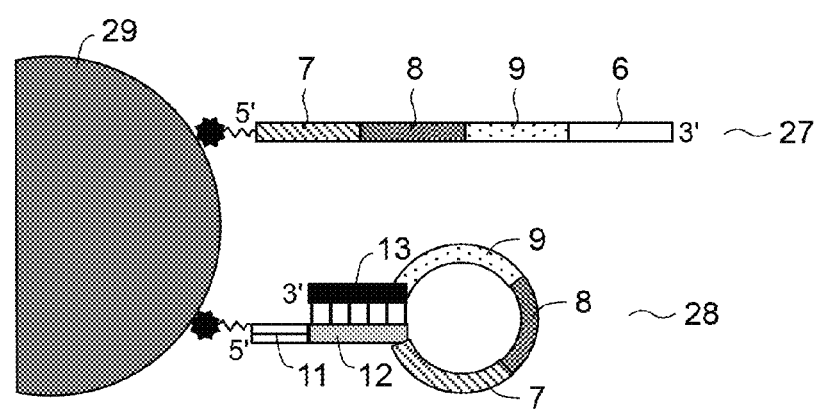

Fig. 8
(a)
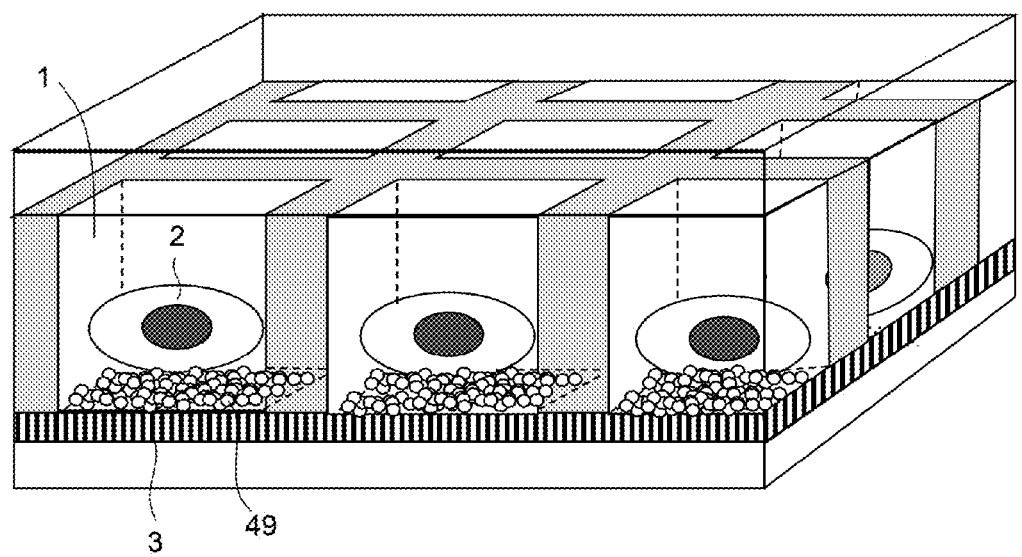
(b)
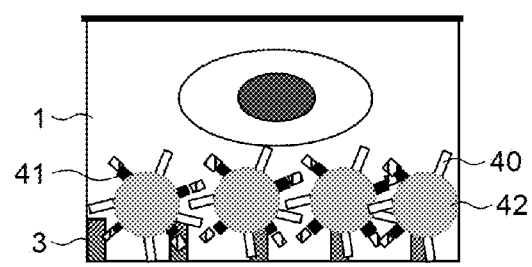
(c)
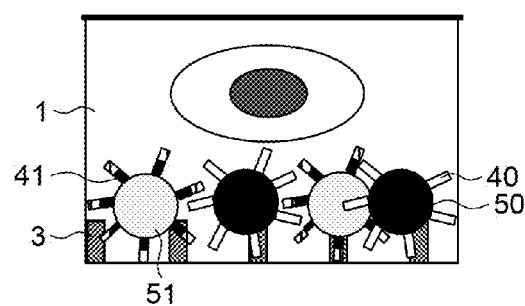

Fig. 10

SEQ ID NO: 5

5' VNCCGCGACGTCCATCTCATCCCTGCGTGTCTCCGACTCAGAGCT
ANNNNNNNACGTCGCGGAGGGGCCATCCACAGTCTTCTGGGTGGCAG
TGATGGCATGGACTGTGGTCATGAGTCCTTCCACGATACCAAAGTTG
TCATGGATGACCTTGGCCAGGGGTGCTAAGCAGTTGGTGGTGCAGGA
GGCATTGCTGATGATCTTGAGGCTGTTGTCATACTTCTCATGGTTCA
CACCCATGACGAACATGGGGGCATCAGCAGAGGGGGCAGAGATGATG
ACCCTTTTGGCTCCCCCCTGCAAATGAGCCCCAGCCTTCTCCATGGT
GGTGAAGACGCCAGTGGACTCCACGACGTACTCAGCGCCAGCATCGC
CCCACTTGATTTTGGAGGGATCTCGCTCCTGGAAGATGGTGATGGGA ~63
TTTCCATTGATGACAAGCTTCCCGTTCTCAGCCTTGACGGTGCCATG
GAATTTGCCATGGGTGGAATCATATTGGAACATGTAAACCATGTAGT
TGAGGTCAATGAAGGGGTCATTGATGGCAACAATATCCACTTTACCA
GAGTTAAAAGCAGCCCTGGTGACCAGGCGCCCAATACGACCAAATCC
GTTGACTCCGACCTTCACCTTCCCCATGGTGTCTGAGCGATGTGGCT
CGGCTGGCGACGCAAAAGAAGATGCGGCTGACTGTCGAACAGGAGGA
GCAGAGAGCGAAGCGGGAGGCTGCGGGCTCAATTT3'

Fig. 12A
(a)
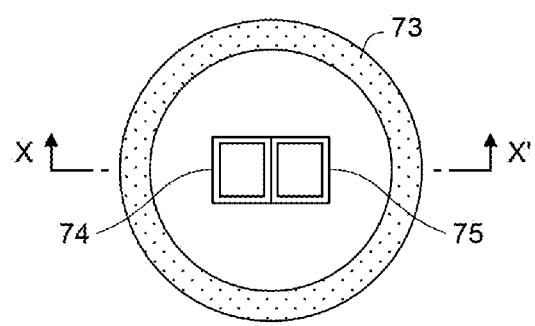
(b)
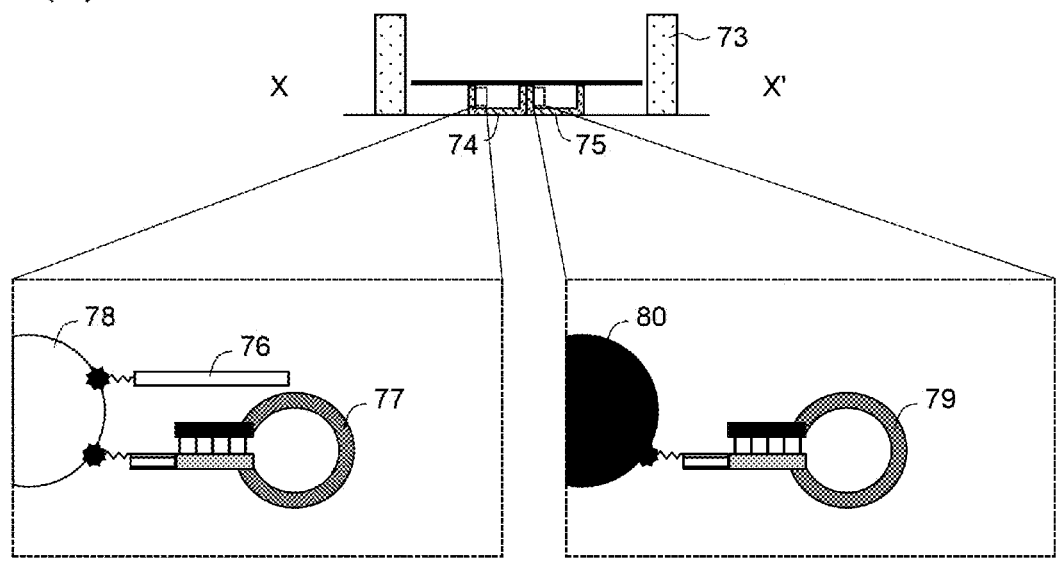

Fig. 12B
(a)
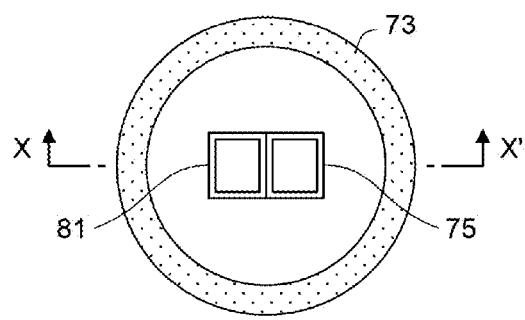
(b)
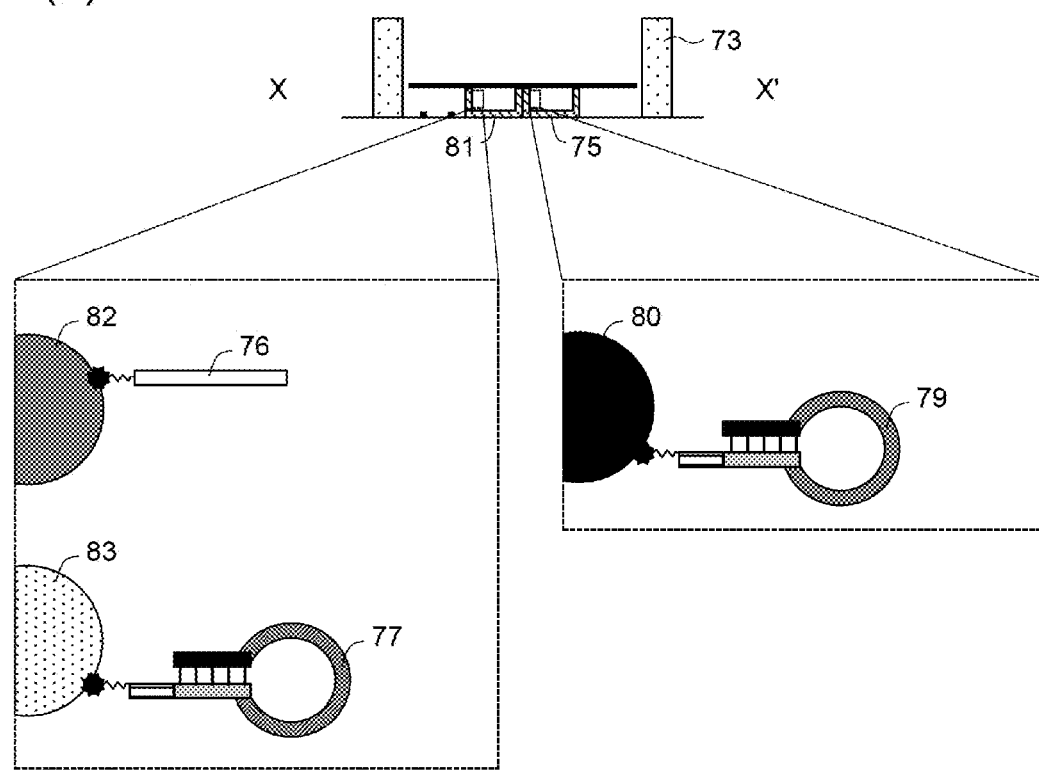

Fig. 12C
(a)
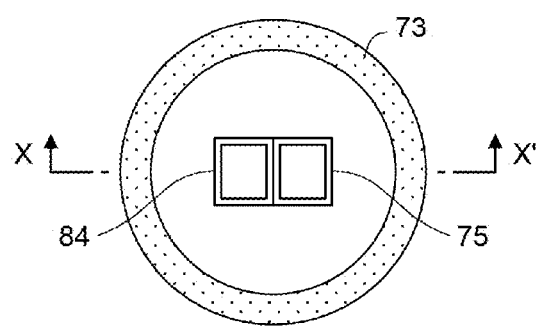
(b)
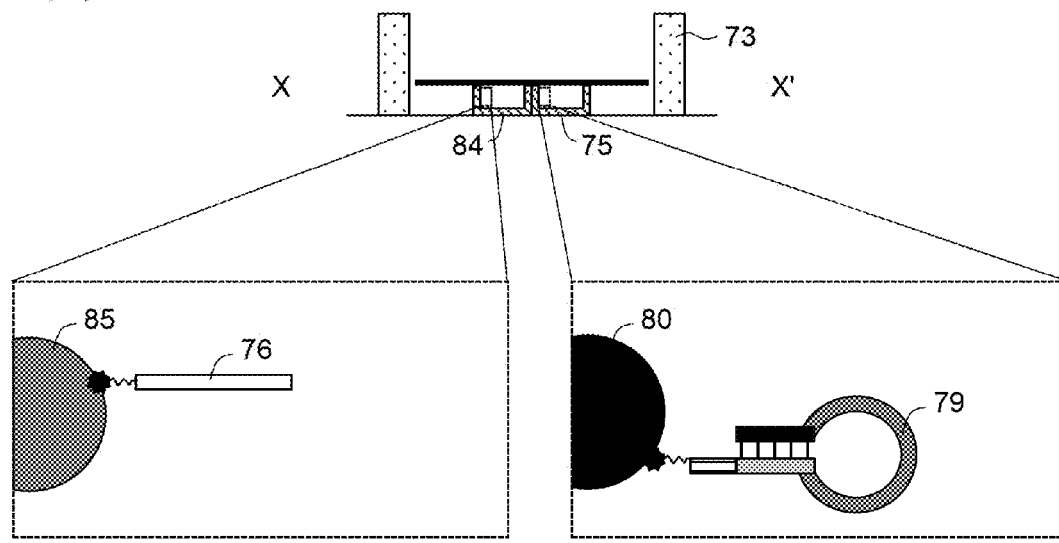

GENETIC ANALYSIS SYSTEM

CROSS REFERENCE TO PRIOR APPLICATIONS

This application is a U.S. National Phase application under 35 U.S.C. §371 of International Application No. PCT/JP2013/078426, filed on Oct. 21, 2013. The International Application was published in Japanese on Apr. 30, 2015 as WO 2015/059741 A1 under PCT Article 21(2). The contents of the above applications are hereby incorporated by reference.

SEQUENCE LISTING

The instant application contains a Sequence Listing which has been submitted electronically in ASCII format and is hereby incorporated by reference in its entirety. Pursuant to 37 C.F.R. §1.52(e)(5), the Sequence Listing text file, identified as 072388_1254_Sequence_Listing.txt, is 6,399 bytes and was created on Apr. 12, 2016. The Sequence Listing, electronically filed herewith, does not extend beyond the scope of the specification and thus does not contain new matter.

TECHNICAL FIELD

The present invention relates to a genetic analysis system. More specifically, the present invention relates to a genetic analysis system capable of analyzing genetic information at a single-cell level.

BACKGROUND ART

Organisms transcribe genetic information stored in the genome to mRNA (gene expression) and synthesize proteins on the basis of the information. Furthermore, the living organisms do life activities by the biological functions of the proteins. In recent years, studies for comprehensive understanding of the living organisms have advanced rapidly by exhaustively analysis of biological functions at a molecular level. By the exhaustive analysis, for example, the functions of pathological cells or immunocytes can be elucidated and applied to the understanding of the causes of diseases or the development of new drugs.

Genome analysis capable of more directly obtaining information on the biological functions, or gene expression analysis based on mRNA expression levels has received attention as a means of conducting the exhaustive analysis. The gene expression analysis mainly has been conducted by using DNA microarray. But in recent years, this analysis is mainly conducted by using a large-capacity DNA sequencer. Usually, cultured cells or tissues, which composed of a large number of cells, are used as analysis samples. However, a gene expression profiles even within homogeneous tissue differs among individual cells or times and is therefore not always the same. Thus, for understanding the functions of a tissue accurately and in detail, it is required to analyze gene expression in each individual cell constituting the tissue and comprehensively grasp the whole tissue on the basis of the information on the gene expression. Nonetheless, an mRNA level derived from a single cell is very small. Therefore, it has heretofore been difficult to conduct the gene expression analysis of each individual cell in a tissue. However, with technical progress in nucleic acid analysis apparatuses, reagents, etc., the analysis of a genome sequence, an mRNA sequence, or a gene expression profiles derived from a single cell has become feasible in recent years (Non Patent Literature 1). Particularly, methods for analyzing gene expression in a single cell using a large-capacity next-generation DNA sequencer have achieved remarkable development. Now, an expression status can be determined in detail as to an enormous number of genes (Non Patent Literatures 2 and 3).

In an organism composed of a large number of cells, these cells do not work each independently, but are involved in each other through the mutual exchange of information. Therefore, for knowing life phenomena in detail, it is required to not only analyze gene expression analysis in a single cell but analyze many cells present in the neighborhood of the cell at the same time and one by one. The number of cells constituting the cell group to be analyzed is several hundreds or in some cases, beyond several tens of thousands. In the case of conducting the gene expression analysis of each individual cell in the cell group, reaction must be carried out in separate reaction vessels by each cell. However, the number of cells that can be analyzed at once relatively easily by a current nucleic acid analysis technique is on the order of several tens of cells. Hence, there has been a demand for a novel technique for extracting nucleic acids such as mRNA on a cell basis from several hundreds or more cells and analyzing the nucleic acids at once.

Patent Literature 1 discloses a method for constructing a complementary-strand DNA (cDNA) library using a porous membrane, etc., as a means for solving the problems described above. In this method, a large number of cells or living tissue sections are located on a membrane, and mRNA can be extracted therefrom under an electric field to construct cDNA library arrays on a cell basis in a multiple regions present immediately beneath the respective cells. In the cDNA library arrays constructed by this method, the cDNA library derived from a single cell is located in each region in a two-dimensional planar form. For analyzing the cDNA library arrays containing multiple regions at once by using a large-capacity DNA sequencer, nucleic acid amplification step and fragmentation step of cleaving DNA into a length convenient for nucleotide sequence analysis are necessary. During the course of these steps, however, reaction products are mixed up among the regions. Therefore, the identity of a cell from the resulting nucleotide sequence information is masked.

CITATION LIST

Patent Literature

Patent Literature 1: JP Patent Publication (Kokai) No. 2009-276883 A (2009)

Non Patent Literature

Non Patent Literature 1: Nature Method vol. 6, no. 7, 503-506 (2009)
Non Patent Literature 2: Nature Biotechnology vol. 30, 763-765 (2012)
Non Patent Literature 3: Cell Reports vol. 2, 666-673 (2012)

SUMMARY OF INVENTION

Technical Problem

An object of the present invention is to solve the problems described above and therefore to develop and provide a genetic analysis system which comprises a multiple regions in which a cDNA library derived from a single cell is located on a region basis, and is capable of identifying reaction products derived from the respective regions even by analysis at once in a nucleic acid amplification step or a fragmentation step. Another object of the present invention is to provide a method for analyzing at once gene expression on a cell basis from a group of several hundreds or more cells using the genetic analysis system.

Solution to Problem

In order to attain the objects, the present inventors have prepared cDNA library arrays comprising multiple regions in which a cDNA library derived from a single cell is located, and developed a novel technique of introducing a tag sequence specific for each region to each fragment after cleaving a complementary DNA strand prepared in each region into a size convenient for analysis with preventing such cleaved fragments from being mixed up among the regions.

Specifically, the present invention encompasses the following:

(1) A genetic analysis system comprising: a substrate comprising one or more cell retention region(s) each capable of retaining a single cell; a first probe comprising a capturing sequence that comprises a sequence complementary to a portion of the nucleotide sequence of a single-strand nucleic acid extracted from the cell retained in the cell retention region and traps the extracted single-strand nucleic acid, and a tag sequence specific to each cell retention region, wherein the first probe is located in the cell retention region; and a second probe comprising a cleaved fragment-complementary sequence that comprises a sequence complementary to a portion of the nucleotide sequence of a cleaved fragment resulting from the cleavage of a complementary strand synthesized by using the single-strand nucleic acid trapped by the first probe as a template, and forms base pairing with the cleaved fragment, and the tag sequence specific to each cell retention region, wherein the second probe is located in the cell retention region.

(2) The genetic analysis system according to (1), wherein the first probe and the second probe each further comprise a common sequence and/or a nucleic acid amplification correction sequence.

(3) The genetic analysis system according to (1) or (2), wherein the cleaved fragment resulting from the cleavage of a complementary strand synthesized by using the single-strand nucleic acid as a template is a cleaved fragment resulting from the cleavage thereof with a restriction enzyme.

(4) The genetic analysis system according to (3), wherein the cleaved fragment-complementary sequence comprises a sequence complementary to a cleaved end after the cleavage with the restriction enzyme.

(5) The genetic analysis system according to any of (1) to (4), wherein the second probe further comprises a stem sense strand consisting of an arbitrary nucleotide sequence, and a stem antisense strand consisting of a nucleotide sequence complementary to the stem sense strand, wherein any one of the stem sense strand and the stem antisense strand is located at the 3' end of the second probe, and the other strand is located adjacent to the 3'-terminal side of the cleaved fragment-complementary sequence positioned at the 5' end of the second probe, and both the strands are hybridized with each other within the second probe to form a stem structure.

(6) The genetic analysis system according to any of (1) to (5), wherein the first probe and/or the second probe is immobilized on a carrier retained on the surface of the cell retention region.

(7) The genetic analysis system according to (6), wherein the first probe and/or the second probe is immobilized on the carrier via a joint molecule.

(8) The genetic analysis system according to (6) or (7), wherein the first probe and the second probe are immobilized on the same carrier or different carriers.

(9) The genetic analysis system according to any of (6) to (8), wherein the 5'-terminal portion of the first probe and/or the second probe is immobilized on the carrier.

(10) The genetic analysis system according to any of (6) to (8), wherein a site other than the terminal portion of the first probe and/or the second probe is immobilized on the carrier.

(11) The genetic analysis system according to any of (1) to (10), wherein the existing density of the first probe and/or the second probe per cell retention region is 5 pM or larger.

(12) The genetic analysis system according to any of (1) to (11), wherein the location of the second probe in the cell retention region is dissociable depending on change in environment.

(13) The genetic analysis system according to (12), wherein the environment is temperature or light.

(14) A genetic analysis method comprising: a first step of supplying multiple cells onto a substrate of a genetic analysis system according to any of (1) to (13) so that the cells are retained one by one in respective cell retention regions; a second step of extracting a nucleic acid from each cell retained in the cell retention region in the first step, and capturing the synthesized single-strand nucleic acid by a first probe in the cell retention region; a third step of using the first probe as a primer and the single-strand nucleic acid trapped in the second step as a template to synthesize a complementary strand thereof, a fourth step of fragmenting the complementary strand synthesized in the third step, and capturing the cleaved fragment in the same cell retention region thereas; and a fifth step of introducing a tag sequence to the trapped cleaved fragment on a cell retention region basis.

(15) The genetic analysis method according to (14), wherein the trapping of the cleaved fragment in the cell retention region in the fourth step is carried out via hybridization to the cleaved fragment-complementary sequence of the second probe.

(16) The genetic analysis method according to (15), wherein the introduction of a tag sequence in the fifth step is carried out via the ligation between the trapped cleaved fragment and the second probe.

(17) The genetic analysis method according to (14), wherein the trapping of the cleaved fragment in the cell retention region in the fourth step is carried out via the binding between joint molecules respectively modifying the inside of the cell retention region and the cleaved fragment.

(18) The genetic analysis method according to (17), wherein the joint molecules are biotin and avidin, streptavidin, or NeutrAvidin.

(19) The genetic analysis method according to (17) or (18), wherein in the fifth step, the tag sequence is introduced to a complementary strand of the cleaved fragment by binding via the hybridization of the cleaved fragment trapped in the cell retention region to the cleaved fragment-complementary sequence of the second probe and by using the second probe as a primer and the cleaved fragment trapped in the second step as a template to synthesize the complementary strand thereof.

Advantageous Effects of Invention

According to the present invention, genetic information on a large number of cells can be analyzed for each individual cell by the same effort as that required for the analysis of a single cell.

Moreover, the present invention can be applied to gene diagnosis, drug development, and the elucidation of diseases such as cancer or regenerative medicine and can also make a contribution to the development of life science.

BRIEF DESCRIPTION OF DRAWINGS

FIG. 1 is a schematic diagram showing one embodiment of substrate construction in the genetic analysis system of the present invention.

FIG. 5 is a diagram showing substrate construction, nucleic acid probe construction, and an immobilization pattern of nucleic acid probes in a genetic analysis system used in Example 2. FIGS. 5(a) and 5(b) show different immobilization patterns of nucleic acid probes to a carrier. FIG. 5(c) shows specific construction of the nucleic acid probes in the immobilization pattern of FIG. 5(a).

FIG. 8 is a diagram showing substrate construction, nucleic acid probe construction, and an immobilization pattern of nucleic acid probes in a genetic analysis system used in Example 3. FIG. 8(a) shows the substrate construction of the genetic analysis system. FIGS. 8(b) and 8(c) show different immobilization patterns of nucleic acid probes to a carrier.

FIG. 10 shows the nucleotide sequence of a binding product used in detection in Example 4.

FIG. 12A is a diagram showing substrate construction and nucleic acid probe construction in one genetic analysis system used in Example 5. FIG. 12A(a) shows the construction viewed from above the genetic analysis system. FIG. 12A(b) is a cross-sectional view taken along the X-X' line in the genetic analysis system of FIG. 12A(a). In FIG. 12A(b), each of the right and left lower diagrams is an enlarged view of a box indicated by a broken line in the upper diagram.

FIG. 12B is a diagram showing substrate construction and nucleic acid probe construction in another genetic analysis system used in Example 5. FIG. 12B(a) shows the construction viewed from above the genetic analysis system. FIG. 12B(b) is a cross-sectional view taken along the X-X' line in the genetic analysis system of FIG. 12B(a). In FIG. 12B(b), each of the right and left lower diagrams is an enlarged view of a box indicated by a broken line in the upper diagram.

FIG. 12C is a diagram showing substrate construction and nucleic acid probe construction in a control genetic analysis system used in Example 5. FIG. 12C(a) shows the construction viewed from above the control. FIG. 12C(b) is a cross-sectional view taken along the X-X' line in the control of FIG. 12C(a). In FIG. 12C(b), each of the right and left lower diagrams is an enlarged view of a box indicated by a broken line in the upper diagram.

DESCRIPTION OF EMBODIMENTS

1. Genetic Analysis System

Figure 2:
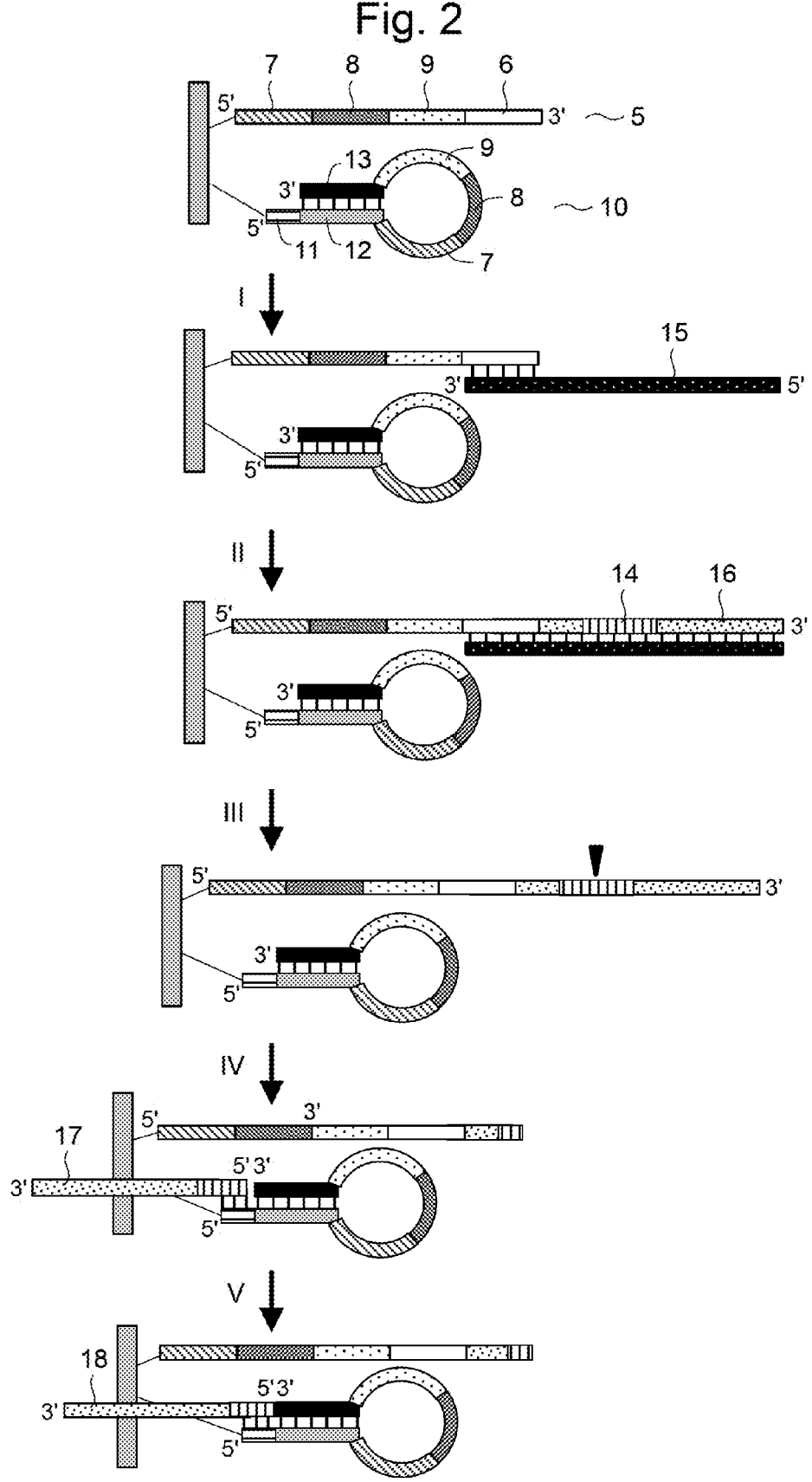
FIG. 2 is a diagram showing one embodiment of nucleic acid probe construction and reaction steps in the genetic analysis system of the present invention.

The construction of the genetic analysis system of the present invention will be described. The genetic analysis system of the present invention is a device comprising a substrate, a first probe, and a second probe as essential components.

1-1. Substrate

The "substrate" in the genetic analysis system of the present invention refers to a support comprising one or more cell retention region(s).

The raw material of the substrate is not particularly limited as long as the substrate is made of a material generally used in the art for the gene expression analysis of DNA and RNA. Examples thereof include: metals consisting of gold, silver, copper, aluminum, tungsten, molybdenum, chromium, platinum, titanium, nickel, and alloys of stainless and the like; silicon; glass materials such as glass, quartz glass, fused quartz, synthetic quartz, alumina, and photosensitive glass (these materials are basically transparent); plastics such as polyester resin, polystyrene, polyethylene resin, polypropylene resin, ABS resin (acrylonitrile butadiene styrene resin), nylon, acrylic resin, and vinyl chloride resin (these materials are generally not transparent, but are desirably rendered transparent for achieving optical measurement); and agarose, dextran, cellulose, polyvinyl alcohol, nitrocellulose, chitin, and chitosan.

The substrate may be made of two or more different raw materials. In the case of, for example, a substrate having a sheet with pores in the bottom of the substrate, such construction corresponds to, for example, the case where the skeleton of the substrate is constituted by the plastic, the metal, or the like, and the sheet with pores is constituted by, for example, an alumina, glass, or silicon film; a thin gel film made of an acrylamide gel, gelatin, modified polyethylene glycol, modified polyvinylpyrrolidone, or hydrogel; or a cellulose acetate membrane, a nitrocellulose membrane, or a mixed membrane thereof, or a nylon membrane.

The substrate can be subjected, if necessary, to processing such as housing. The substrate is preferably prepared from a material transparent to, i.e., permeable to, light at least some wavelengths of light wavelengths from 300 nm to 10000 nm. This is because the analysis of gene expression can be optically conducted on the substrate.

The "cell retention region" is a compartment consisting of very small space located in the substrate and is configured that multiple cells supplied to the substrate can be retained one by one in respective cell retention regions. The shape of the cell retention region is not particularly limited. The shape corresponds to, for example, a cylindrical shape, a nearly cylindrical shape, an elliptic cylindrical shape, a nearly elliptic cylindrical shape, a rectangular shape, a nearly rectangular shape, a cubic shape, a nearly cubic shape, a conical shape, a nearly conical shape, a pyramidal shape, or a nearly pyramidal shape. The opening diameter of the cell retention region can be from a size slightly smaller than the diameter of a cell to a size in which a single-cell fits comfortably. The opening diameter can be, for example, in the diameter range of 5 µm to 50 µm. The depth of the cell retention region can be from 1 µm to a depth in which a single-cell fits comfortably, for example, in the range of 5 to 100 µm. The number of the cell retention region per substrate is not particularly limited. The number of the cell retention region may be one or may be two or more. Usually, the number of the cell retention region can be in the range of 10 to $10^5$. The cell retention region functions as a reaction vessel in the substrate.

The inside of the cell retention region has a first probe and a second probe mentioned later.

1-2. First Probe

In the genetic analysis system of the present invention, the "first probe" is a probe constituted by a nucleic acid. The first probe is constituted by DNA as a rule, though the first probe is not limited thereto. The first probe may contain, for example, RNA or an artificial nucleic acid.

The first probe comprises a capturing sequence and a tag sequence and is located in the cell retention region. The first probe, if necessary, further comprises a common sequence and/or a nucleic acid amplification correction sequence. Hereinafter, each sequence constituting the first probe will be described specifically.

The "capturing sequence", which is an essential sequence constituting the first probe, comprises a sequence complementary to a portion of the nucleotide sequence of a single-strand nucleic acid extracted from the cell retained in the cell retention region, or a random sequence and is constructed to trap the extracted single-strand nucleic acid. The nucleotide sequence of the capturing sequence is not particularly limited as long as the capturing sequence can be hybridized with the single-strand nucleic acid as a target to trap it. Hence, the capturing sequence can be appropriately designed in consideration of the type and sequence of the nucleic acid. In the present invention, examples of the single-strand nucleic acid as a target include messenger RNA (mRNA), non-coding RNA (ncRNA), microRNA, and single-strand DNA, and their fragments. The length of the capturing sequence can be a length that enables trapping of the single-strand nucleic acid as a target by hybridization. The capturing sequence is preferably a sequence complementary to the 3'-terminal side or its adjacent sequence in the nucleotide sequence of the single-strand nucleic acid.

When the single-strand nucleic acid as a target is, for example, mRNA, an oligo (dT) sequence complementary to a poly-A sequence which is a portion of the sequence of the mRNA, is preferably used as the capturing sequence. The length of polymerization of dT constituting the oligo (dT) sequence can be the length that enables trapping of the poly-A sequence of the mRNA by hybridization. The length of polymerization is, for example, 8 to 40, preferably 8 to 30. In the case of using an oligo (dT) sequence as the capturing sequence, it is preferred to add a 2-base random sequence to the 3' end thereof. This can drastically reduce the amount of artifacts during the synthesis of cDNA. Examples of such a random sequence include VN sequences (wherein V is A, G, or C, and N is A, G, C, or T).

When the single-strand nucleic acid as a target is a single-strand nucleic acid derived from microRNA or genomic DNA, a sequence complementary to a portion of the nucleotide sequence of the single-strand nucleic acid, or a random sequence can be used.

The "tag sequence", which is an essential sequence constituting the first probe, is an identification tag to be introduced to a reaction product in the cell retention region. Thus, when multiple cell retention regions are present, the tag sequence comprises a nucleotide sequence specific to each cell retention region. The tag sequence is constituted by a known nucleotide sequence with arbitrary length. When the tag sequence is, for example, 5 bases long, $4^5$ (=1024) different types of tag sequences specific to the cell retention regions can be applied thereto. Likewise, when the tag sequence is, for example, 10 bases long, $4^{10}$ (=1048576) different types of tag sequences specific to the cell retention regions can be applied thereto. Thus, the length of the tag sequence can be appropriately determined according to the position and/or the number of the cell retention region in the genetic analysis system so that the cell retention region can be identified. Specifically, the length is preferably 5 to 30 bases.

When multiple cell retention regions are present in the substrate, the nucleotide sequence constituting the tag sequence differs among the cell retention regions as a rule, but may be common in multiple cell retention regions, if necessary. The latter case corresponds to, for example, the case where a common tag sequence is used in five cell retention regions in one substrate. In this case, these five cell retention regions using the common tag sequence can also be regarded as a single cell retention region.

The "common sequence", which is an optional sequence, is a sequence capable of functioning as a forward (Fw) primer sequence for the amplification of a cleaved fragment in a nucleic acid amplification step of a genetic analysis method using the genetic analysis system of the present invention. Thus, the common sequence is located on the 5'-terminal side in the first probe as a rule. The base length of the common sequence is not particularly limited as long as the length is appropriate as a primer. The common sequence can be, for example, 8 to 60 bases long, preferably 10 to 50 bases long. The nucleotide sequence of the common sequence is not particularly limited, and the common sequence is preferably designed as a sequence that offers a Tm value appropriate for a primer sequence. Usually, the nucleotide sequence is designed such that the Tm value is 50° C. or higher, preferably 60° C. or higher.

The "nucleic acid amplification correction sequence" is a sequence that corrects an amplification bias in a nucleic acid amplification step of a genetic analysis method using the genetic analysis system of the present invention. In general, in the nucleic acid amplification step, the amplification efficiency of each nucleic acid fragment is biased depending on conditions such as the length, the sequence and the position of the nucleic acid fragment to be amplified. Therefore, it is difficult to perform the accurate quantification of an amplification product. In the method of the present invention, different nucleic acid amplification correction sequences are introduced to individual nucleic acid fragments. Therefore, multiple data with the same nucleic acid amplification correction sequence can be regarded as being derived from the same cleaved fragment and corrected for sequence analysis. Hence, the amplification bias that has occurred in each step can be corrected. The base length of the nucleic acid amplification correction sequence is not particularly limited. The base length can be in the range of, for example, 5 to 30 bases, preferably 10 to 20 bases, more preferably 10 to 15 bases. The nucleotide sequence of the common sequence is not particularly limited as long as the nucleotide sequence has a random sequence. The nucleotide sequence may have a known sequence or may have an unknown sequence.

As for the position of the capturing sequence, the tag sequence, the common sequence, and the nucleic acid amplification correction sequence in the first probe, the capturing sequence is located on the 3'-terminal side of the first probe, and the common sequence is located on the 5'-terminal side of the first probe, though the position of the other sequences is not particularly limited.

The first probe and the second probe mentioned later (in the present specification, these probes are sometimes referred to as "nucleic acid probes" collectively) are located in the cell retention region. The nucleic acid probes are located in advance in the cell retention region, whereby genetic information can be accrued from nucleic acids derived from individual cells without damaging cells or tissues and without using a robot or the like. Particularly, this approach causes no damage on cells or tissues and can therefore eliminate the problem of gene expression change caused by such damage.

In this context, the term "located" refers to direct and/or indirect immobilization to a predetermined position by an appropriate method.

Examples of the direct immobilization of each nucleic acid probe in the cell retention region include immobilization on the inner surface of the cell retention region. The immobilization position is not limited. The inner surface may be, for example, the bottom surface or wall surface of the cell retention region, or a combination thereof, or the entire surface. In this context, when the cell retention region has a sheet with pores, the inner surface of the pores or the fiber surface of the sheet is also included in the inner surface of the cell retention region.

Examples of the indirect immobilization of the first probe in the cell retention region include immobilization on the surface of a carrier retained by the surface of the cell retention region. In the present specification, the "carrier" is an intervening substance that links each nucleic acid probe to the cell retention region. The nucleic acid probe is immobilized on the surface thereof, and the carrier itself is also immobilized, if necessary in a dissociable state, on the inner surface of the cell retention region. The raw material of the carrier is not limited. The carrier is constituted by, for example, a resin material (polystyrene, etc.), an oxide (glass, silica, etc.), a metal (iron, gold, platinum, silver, etc.), a macromolecular polysaccharide support (e.g., Sepharose or Sephadex), ceramic, latex, or a combination thereof. The shape of the carrier is not particularly limited, and spherical particles such as beads are preferred because of a large binding surface area and high operability. Hence, magnetic beads are suitable as the carrier.

The nucleic acid probes are located in the cell retention region by any immobilization method known in the art. Examples of the immobilization method include biological binding, covalent binding, ionic binding, and physical adsorption to the inner surface of the cell retention region or the surface of the carrier. Alternatively, both the probes may be immobilized on the inner surface of the cell retention region or the carrier via a spacer sequence.

Examples of the biological binding include joint molecule-mediated binding such as the binding between biotin and avidin, streptavidin, or NeutrAvidin, and antigen-antibody binding. The biological binding can be achieved, for example, by reacting a biotinylated nucleic acid probe with avidin-, streptavidin-, or NeutrAvidin-bound inner surface of the cell retention region.

The covalent binding can be achieved, for example, by introducing a functional group to each nucleic acid probe, introducing a functional group reactive with the functional group to the inner surface of the cell retention region, and reacting them. Specifically, for example, an amino group is introduced to the nucleic acid probe, and an active ester group, an epoxy group, an aldehyde group, a carbodiimide group, an isothiocyanate group, or an isocyanate group is introduced to the inner surface of the cell retention region so that a covalent bond can be formed therebetween. Alternatively, a mercapto group may be introduced to the first probe, and an active ester group, a maleimide group, or a disulfide group may be introduced to the inner surface of the cell retention region. Examples of the method for introducing the functional group to the inner surface of the cell retention region or the surface of the carrier include a method which involves treating the inner surface of the cell retention region with a silane coupling agent having the desired functional group. For example, γ-aminopropyltriethoxysilane, N-β-(aminoethyl)-γ-aminopropyltrimethoxysilane, or N-β-(aminoethyl)-β-aminopropylmethyldimethoxysilane can be used as the coupling agent. Another example of the method for introducing the functional group to the inner surface of the cell retention region or the surface of the carrier includes plasma treatment.

Examples of the physical adsorption include a method which involves surface-treating the inner surface of the cell retention region with a polycation (polylysine, polyallylamine, polyethylenimine, etc.) and forming an electrostatic bond by use of the electric charge of the nucleic acid probe. The inside of the cell retention region or the carrier is preferably surface-coated in advance so as to prevent other substances (nucleic acids, proteins, etc.) from being adsorbed thereon.

1-3. Second Probe

In the genetic analysis system of the present invention, the "second probe" is a probe constituted by a nucleic acid, as with the first probe. The second probe is also constituted by DNA as a rule, though the second probe is not limited thereto. The second probe may contain, for example, RNA or an artificial nucleic acid.

The second probe comprises a cleaved fragment-complementary sequence and a tag sequence as essential sequences and is located in the cell retention region. The second probe, if necessary, can further comprise a common sequence, a nucleic acid amplification correction sequence, and a stem sense sequence, and a stem antisense sequence.

The "cleaved fragment-complementary sequence" comprises a sequence complementary to a portion of the nucleotide sequence of a cleaved fragment and is constructed so as to form hybridizing with the cleaved fragment. In this context, the "cleaved fragment" refers to a nucleic acid fragment resulting from the cleavage of complementary strand synthesized by using the single-strand nucleic acid trapped by the first probe as a template. If necessary for cleavage, the cleavage sequence or the complementary strand synthesized by using the trapped single-strand nucleic acid as a template may be modified so as to be cleavable.

The cleavage of the complementary strand can be carried out by a method known in the art. Examples thereof include cleavage with a restriction enzyme, and a method which involves applying thereto light with specific wavelength or vibration (ultrasonic wave).

In the cleavage using a restriction enzyme, an enzyme capable of cleaving any DNA strand in double-strand DNA, single-strand DNA, or a DNA/RNA strand is used. When the trapped single-strand nucleic acid is, for example, RNA such as mRNA, a restriction enzyme that can cleave only a DNA strand in a double-strand DNA/RNA hybrid strand consisting of the RNA and a complementary DNA strand synthesized by using the RNA as a template may be used. Examples of such a restriction enzyme include BstNI. Alternatively, only the trapped RNA strand in the DNA/RNA hybrid strand is removed by degradation with RNase H or the like, and a restriction enzyme that can cleave the remaining single-strand DNA may be used. Examples of such a restriction enzyme include AccI, AccII, AvaII, BspRI, CfoI, DdeI, EcoRI, HaeIII, HpaII, HhaI, HinfI, MspI, MboI, MboII, Sau3AI, SfaI, and TthHB81. When the trapped single-strand nucleic acid is DNA, a restriction enzyme that can cleave double-strand DNA consisting of the DNA and a complementary DNA strand synthesized by using the DNA as a template can be used. More preferably, a restriction enzyme (enzyme creating a nick) that can cleave only one of the DNA strands in the double-strand DNA is used.

The restriction enzyme recognizes and cleaves a unique cleavage sequence present on a nucleic acid. Thus, for obtaining the length of the cleaved fragment suitable for sequence analysis, it is desirable that the sequence that can be cleaved by the restriction enzyme should be the length of 4 or 5 bases sequence or multiple restriction enzymes should be combined, though the present invention is not limited thereto. The cleaved fragment-complementary sequence comprises at least a portion of a complementary sequence of the cleavage sequence. The 5' end of a portion of the complementary strand of the cleavage sequence may be provided with a mixed base VN or may be provided with a portion of a specific sequence for the cleaved fragment.

In one embodiment, ultrasonic wave may be used as a means for cleavage. In this case, a complementary sequence of a specific sequence in the cleaved fragment to be trapped, or a sequence comprising the end of a site to be cleaved can be used as the cleaved fragment-complementary sequence in the first probe to thereby realize hybridization reaction and subsequent reactions. For example, the 3' side is used as a portion of the cleaved fragment-complementary sequence, and this sequence uses a protruding end of stem structure. As a result, a nick is formed during the hybridization between the recognizing probe and the cleaved fragment. DNA ligase binds to this nick so that the recognizing probe can be bound to the cleaved fragment.

Photoligation may be used as a means for binding the second probe to the cleaved fragment. In this case, a 3'-terminal base of the complementary sequence of an arbitrary sequence in the recognizing probe is replaced with an artificial synthetic base, and the resulting probe can be bound with the cleaved fragment by irradiation with light having a wavelength of 366 nm after hybridization (Organic Letters 7. 2853-2856).

The "tag sequence" has the same construction as that of the tag sequence described in the first probe, so that the specific description is omitted here. Since the tag sequence is, as mentioned above, an identification tag that indicates being derived from the same cell retention region, the tag sequences of the first probe and the second probe located in a single cell retention region are constituted by the same sequence as a rule.

The "common sequence", which is an optional sequence, is a sequence capable of functioning as a reverse (Rev) primer sequence for the amplification of the cleaved fragment in a nucleic acid amplification step of a genetic analysis method using the genetic analysis system of the present invention, and basically has the same construction as that of the common sequence described in the first probe. However, the position of the common sequence in the second probe is not necessarily required to be a position on the 5'-terminal end.

The "nucleic acid amplification correction sequence" has the same construction as that of the nucleic acid amplification correction sequence described in the first probe, so that the specific description is omitted here.

The "stem sense sequence and stem antisense sequence", which are optional sequences unique to the second probe, consist of nucleotide sequences complementary to each other. The base lengths of these sequences are the same with each other as a rule. The lengths are not particularly limited as long as both the sequences can form a stable stem structure. The base lengths can be in the range of, for example, 3 to 7 bases. The nucleotide sequence constituting each sequence is not particularly limited as long as the sequences are complementary to each other.

In the second probe, a pair of the stem sense sequence and the stem antisense sequence is present in a state of separation by an arbitrary nucleotide sequence located therebetween. The arbitrary nucleotide sequence comprises at least the tag sequence and can also comprise the common sequence and/or the nucleic acid amplification correction sequence. The stem sense sequence and the stem antisense sequence can be hybridized with each other within the second probe to form a stem structure. This structure allows the arbitrary sequence to be a loop structure and the second probe to form a loop-stem structure as a whole. The resulting second probe assumes a structure in which the cleaved fragment-complementary sequence located on the 5' end of the loop-stem structure protrudes. After hybridization with the cleaved fragment, a nick is formed between the double-strand hybridized region and the stem structure. DNA ligase binds to this nick so that the recognizing probe can be bound to the cleaved fragment.

2. Genetic Analysis Method

The genetic analysis method of the present invention will be described. The genetic analysis method of the present invention employs the genetic analysis system of the present invention.

The genetic analysis method of the present invention comprises at least 5 steps: a first step (cell retention step), a second step (single-strand nucleic acid trapping step), a third step (complementary strand synthesis step), a fourth step (complementary strand fragment trapping step), and a fifth step (tag sequence introduction step). Hereinafter, each step will be described.

(First Step)

The "first step: cell retention step" is the step of supplying multiple cells onto the substrate of the genetic analysis system of the present invention so that the cells are retained one by one in respective cell retention regions.

In the present invention, the sample for use in the analysis is not particularly limited as long as the sample is derived from a living organism whose gene expression is to be analyzed. Any sample such as a cell sample, a tissue sample, or a liquid sample can be used. Specific examples thereof include a sample consisting of a single-cell, a sample containing multiple cells, a tissue section sample, and a sample in which multiple individual cells are arranged in a two-dimensional array pattern.

The biomaterial is not particularly limited, and biomaterial derived from any living organism such as a vertebrate (e.g., a mammal, a bird, a reptile, fish, and an amphibian), an invertebrate (e.g., an insect, a nematode, and a crustacean), a protist, a plant, a fungus, a bacterium, or a virus can be used.

(Second Step)

The "second step: single-strand nucleic acid trapping step" is the step of extracting a nucleic acid from each cell retained in the cell retention region in the first step, and trapping the extracted single-strand nucleic acid by the first probe in the cell retention region.

In the second step, the single-strand nucleic acid extracted from the cell retained in the underlying cell retention region is trapped through hybridization by the first probe located in the cell retention region.

In this step, examples of the single-strand nucleic acid as a target to be trapped include, but are not limited to, messenger RNA (mRNA), non-coding RNA (ncRNA), microRNA, and single-strand DNA in cells constituting living tissues, and their fragments. The extraction of the nucleic acid from the cell can be carried out by a method known in the art. For example, the cell can be lysed using a proteolytic enzyme such as proteinase K, a chaotropic salt such as guanidine thiocyanate-guanidine hydrochloride, a surfactant such as Tween or SDS, or a commercially available reagent for cell lysis to elute a nucleic acid, i.e., DNA or RNA, contained therein.

(Third Step)

The "third step: complementary strand synthesis step" is the step of using the first probe as a primer and the single-strand nucleic acid trapped in the second step as a template to synthesize a complementary strand thereof.

In the third step, the complementary strand is synthesized with reverse transcriptase or DNA polymerase by using the first probe as a primer and the trapped nucleic acid as a template.

In the present invention, the synthesis of the complementary strand can be carried out by a method known in the art. When the nucleic acid is, for example, RNA such as mRNA, cDNA can be synthesized, for example, by reverse transcription reaction using reverse transcriptase. When the nucleic acid is DNA, cDNA can be synthesized, for example, by replication reaction using DNA polymerase.

(Fourth Step)

The "fourth step: complementary strand fragment trapping step" is the step of fragmenting the complementary strand synthesized in the third step, and capturing the cleaved fragment in the same cell retention region thereas.

The method for fragmenting the complementary strand may employ a restriction enzyme or may be based on physical stimulation such as ultrasonic wave. The cleavage of the complementary strand can be carried out by a method known in the art. When the single-strand nucleic acid as a template is, for example, RNA such as mRNA, a DNA/RNA hybrid strand is produced after the third step. In this case, the cleavage sequence in the complementary strand can be cleaved with a restriction enzyme that can cleave the DNA strand, which corresponds to the complementary strand, in the DNA/RNA hybrid strand, or a restriction enzyme that can cleave single-strand DNA obtained by RNase H treatment. When the single-strand nucleic acid as a template is DNA, double-strand DNA is produced after the third step. In this case, a restriction enzyme that can cleave the double-strand DNA can be used. More preferably, a restriction enzyme that can cleave only one of the DNA strands in the double-strand DNA (i.e., create a nick) is used. Alternatively, a method without the use of the enzyme as mentioned above, for example, a method for applying thereto light with a specific wavelength or vibration (ultrasonic wave), may be used as the cleavage method. If necessary for cleavage, the cleavage sequence or the modification so as to be cleavable can be introduced to cleaved complementary strand.

The cleaved fragment resulting from the fragmentation of the complementary strand is trapped in the same cell retention region thereas.

Examples of the method for capturing the cleaved fragment include a method using hybridization to the cleaved fragment-complementary sequence of the second probe located in the same cell retention region thereas. Another example of the method for capturing the cleaved fragment includes a method using direct trapping by the inner surface of the cell retention region adjacent the nucleic acid probes, or the carrier retained in the cell retention region. In this case, the inner surface of the cell retention region or the carrier, and the cleaved fragment can be modified such that the cleaved fragment can be trapped. Examples of such modification include a method which involves modifying the nucleic acid probe-immobilized surface of the cell retention region or carrier with avidin, streptavidin, or NeutrAvidin, and biotinylating the cleaved fragment for trapping.

(Fifth Step)

The "fifth step: tag sequence introduction step" is the step of introducing a tag sequence to the trapped cleaved fragment on a cell retention region basis.

In the fifth step, the cleaved fragment trapped by the second probe through hybridization in the fourth step is bound to the second probe so that a tag sequence specific to each cell retention region is introduced to the cleaved fragment. DNA ligase is used in the binding between the second probe and the cleaved fragment. The DNA ligase preferably binds to nick DNA, though the DNA ligase is not limited thereto. The binding between the second probe and the cleaved fragment is not particularly limited as long as the binding is achieved by a means capable of binding nucleic acids. For example, a photoligation method may be used in the binding between the cleaved fragment and the second probe (Angewandte Chemie Int. Ed. 2006, 45, 4512). In this case, a cleaved fragment-binding 3'-terminal end base of the recognizing probe is modified, and the binding can be carried out by irradiation at a specific wavelength. In the case of capturing the cleaved fragment into the cell retention region by its modification, the trapped cleaved fragment is hybridized with the cleaved fragment-complementary sequence contained in the second probe and then the complementary strand is synthesized with DNA polymerase by using the second probe as a synthesis initiation point and the cleaved fragment as a template. By this reaction, the sequence derived from the cleaved fragment is introduced to the second probe. As a result, the tag sequence specific to the cell retention region can be introduced to the cleaved fragment. Then, the whole or a portion of the second probe-introduced cleaved fragment is amplified. In the amplification step, first, a primer comprising a sequence specific for the nucleic acid to be analyzed is annealed to the DNA hybridized with the second probe retained by the inner surface of the cell retention region or the carrier to synthesis a complementary strand comprising a portion of the cleaved fragment and each sequence contained in the second probe mentioned above. A common primer sequence (e.g., a common reverse primer sequence is different from a common forward primer sequence contained in the second probe) corresponding to the common sequence contained in the second probe mentioned above is introduced to the 5' end of the primer, whereby the subsequent amplification step can be carried out conveniently and efficiently. Any method known in the art can be used as the amplification method. Examples thereof include polymerase chain reaction (PCR), nucleic acid sequence-based amplification (NASBA), loop-mediated isothermal amplification (LAMP), and rolling circle amplification (RCA) reaction. Those skilled in the art can appropriately design the second probe used according to adopted amplification reaction.

The product obtained by the fifth step of the present invention is used as a template in nucleic acid amplification. The gene sequence of the amplification product can be analyzed by any method known in the art. Alternatively, gene expression analysis may be conducted by sequence analysis. In one embodiment, for example, the amplification product can be sequenced to analyze the presence or absence of the expression of the gene to be analyzed, its expression level (which is corrected on the basis of the nucleic acid amplification correction sequence), etc. In an alternative embodiment, a labeled probe with a complementary sequence to the gene-specific sequence mentioned above is used, and the probe is hybridized to the cDNA or the obtained amplification product so that the gene expression to be analyzed can be detected (e.g., optically detected) on the basis of the label. Those skilled in the art can appropriately design the probe for use in such detection. As for the label used, any label known in the art can be used. Examples thereof include fluorescent labels (Cy3, fluorescein isothiocyanate (FITC), tetramethylrhodamine isothiocyanate (TRITC), etc.), chemiluminescent labels (luciferin, etc.), enzymatic labels (peroxidase, β-galactosidase, alkaline phosphatase, etc.), and radiolabels (tritium, iodine$^{125}$, etc.). In a further alternative embodiment, a probe with a complementary sequence to the gene-specific sequence mentioned above is used in nucleic acid amplification reaction so that the presence or absence of amplicon can be detected on the basis of chemiluminescence or fluorescence to analyze the expression of the gene to be analyzed.

In the present invention, the genetic analysis results obtained from the cDNA may be associated with two-dimensional positional information on the sample (a cell, a tissue, etc.) to obtain correlation data on a specific position and gene expression in the cell or the tissue. Such two-dimensional positional information on the sample is, for example, a microscope image of a cell sample or a tissue section sample, or a fluorescent or chemiluminescent image obtained by any other labeling method.

EXAMPLES

Hereinafter, the embodiments of the present invention will be described specifically. However, these Examples are given merely for illustrative purposes in order to achieve the present invention and are not intended to limit the present invention.

Example 1

This Example employs a substrate with multiple separated cell retention regions shown in FIG. 1(a), and a genetic analysis system in which a first probe and a second probe shown in FIG. 2 are located in each of the cell retention regions, and shows an example where a cleaved fragment of a complementary strand synthesized by using single-strand nucleic acids derived from a single-cell as a template, which is trapped by the first probe, is ligated to the second probe with DNA ligase.

The substrate of this construction example is constructed such that each cell retention region retains a single cell. A cell retention regions (1) consist of penetrating-pore with an aperture equivalent to or larger than the diameter of a cell (2) and on the order of 20 to 50 µm in terms of diameter, and a porous membrane (3) at the bottom.

In this Example, it is assumed that the single-strand nucleic acid extracted from the cell is mRNA. Hence, a first probe (5) consisting of the nucleotide sequence represented by SEQ ID NO: 1 comprises a capturing sequence (6) consisting of a 12-base oligo (dT) sequence and a 2-base VN sequence on the 3'-terminal side. Additionally, the first probe consists of a 30-base common sequence (7), a 5-base tag sequence (8), and a nucleic acid amplification correction sequence (9) consisting of a 7-base random sequence, in this order from the 5'-terminal side. On the other hand, a second probe (10) consisting of the nucleotide sequence represented by SEQ ID NO: 2 is constituted by a cleaved fragment-complementary sequence (11) consisting of a mixed base VN and 3 bases, a 6-base stem sense sequence (12), a 30-base common sequence (7), a 5-base tag sequence (8), a nucleic acid amplification correction sequence (9) consisting of a 7-base random sequence, and a 6-base stem antisense sequence (13), in this order from the 5' end. In this context, the 3 bases constituting the cleaved fragment-complementary sequence consist of "CCG", which is a sequence complementary to a cleaved end after MspI- or HpaII-mediated cleavage of "CCGG" serving as a recognition sequence for enzymes. MspI and HpaII can cleave single- and double-strand DNA. The stem sense sequence (12) and the stem antisense sequence (13) are hybridized with each other to form a stem, and the common sequence (7), the tag sequence (8), and the nucleic acid amplification correction sequence (9), which positioned between the stem sense sequence (12) and the stem antisense sequence (13), form a loop structure. As a result, the cleaved fragment-complementary sequence (11) positioned at the 5' end of the second probe forms a protruding end. In this Example, the intended restriction enzyme MspI or HpaII of the cleaved fragment-complementary sequence (11) is used, though the restriction enzyme is not limited thereto.

As shown in FIG. 2, reaction steps using the genetic analysis system of this Example, consist of: a single-strand nucleic acid trapping step (I) of hybridizing mRNA (15), which is the single-strand nucleic acid extracted from the cell, to the capturing sequence (6) of the first probe (5) to trap the mRNA; a complementary strand synthesis step (II) of synthesizing cDNA (16) by using the trapped mRNA (15) as a template and the 3' end of the first probe (5) as a synthesis initiation point; a degradation step (III) of degrading the mRNA (15) as the trapped single-strand nucleic acid; a cleaved fragment trapping step (IV) of cleaving (indicated by arrowhead) the synthesized cDNA (16) with a restriction enzyme MspI or HpaII capable of cleaving single-strand DNA, and immediately hybridizing the resulting cleaved fragment (17) to the cleaved fragment-complementary sequence (11) of the second probe (10) to trap the cleaved fragment; and a binding step (V) of binding the 3' end of the second probe (10) to the 5' end of the trapped cleaved fragment (17) with DNA ligase.

Figure 3:
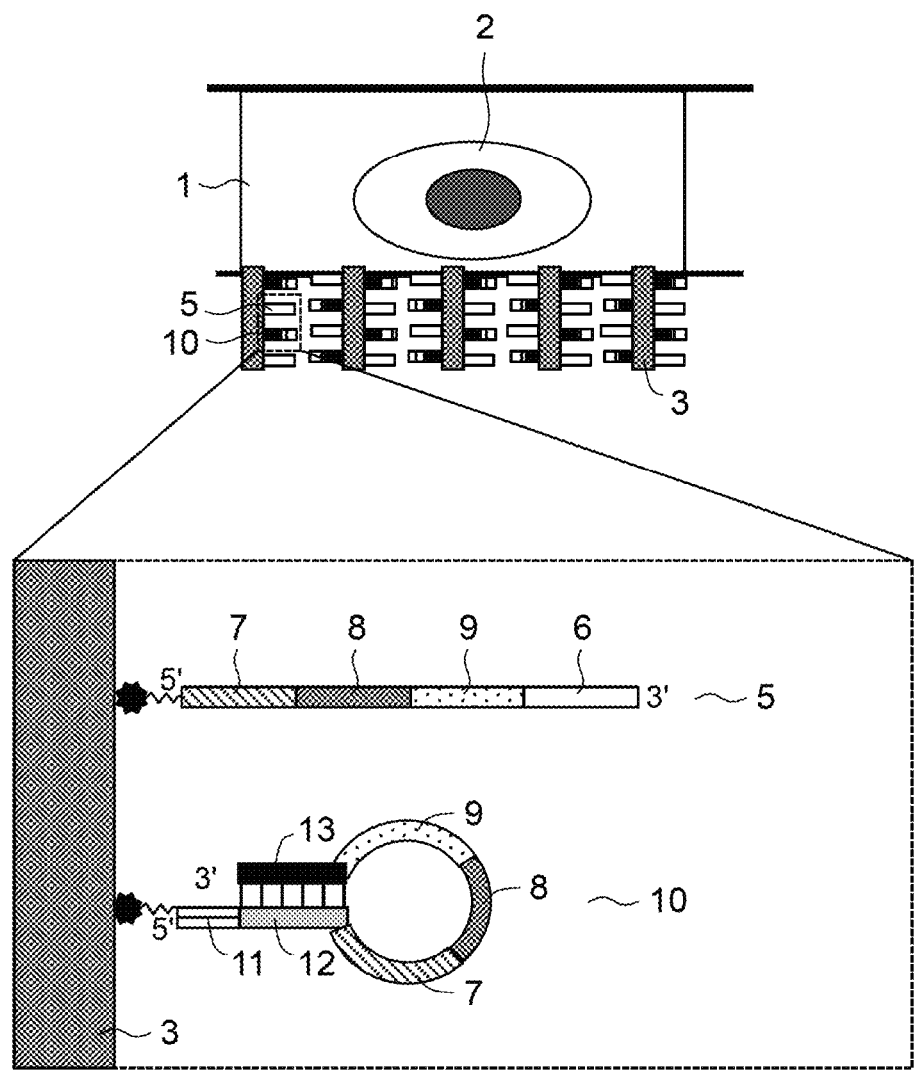
FIG. 3 is a diagram showing substrate construction, nucleic acid probe construction, and an immobilization pattern of nucleic acid probes in a genetic analysis system used in Example 1. The lower diagram is an enlarged view of a box indicated by a broken line in the upper diagram.

Next, construction in which the first probe and the second probe are immobilized in the cell retention region (1) is shown in FIG. 3. FIG. 3 shows an example where the first probe (5) and the second probe (10) are immobilized on the pore surface of the porous membrane (3) constituting the bottom of the cell retention region (1). The 5' end of each nucleic acid probe is modified with an amino group for immobilization. In this Example, commercially available Anodisc (GE Healthcare Japan Corp.) with a pore size on the order of 0.1 to 0.2 μm is used as the porous membrane. The thickness of the porous membrane is 60 μm, and its surface permits immobilization of the nucleic acid probes. Usually, the density of nucleic acid probes that can be immobilized on solid surface is one nucleic acid probe/30 to 100 nm$^2$, and approximately 5×10$^5$ nucleic acid probes can be immobilized on one pore. The volume of each pore is approximately 1.8×10$^{-16}$ L. Thus, the density of the nucleic acid probes is 5 mM. Provided that the ratio of the nucleic acid probes immobilized on the porous membrane is first probe:second probe=approximately 1:5, the densities of the first probe and the second probe are approximately 0.8 mM and approximately 4 mM, respectively, both of which are concentrations sufficient for carrying out reaction with high efficiency and are expected to offer 0% or less probability of losses of cleaved fragments to other cell retention regions (Biophysical journal 69. 2243-2255 (1995); Biophysical journal 20. 193-219 (1997); and Biophysical journal 66. 255-600 (1994)). This ratio may be changed depending on each experimental condition and is not limited thereto.

In this Example, a silane coupling agent for immobilizing the nucleic acid probes (5 and 10) onto the porous membrane (3), and a silanated MPC polymer for preventing protein adsorption were immobilized at an appropriate ratio on the pore surface through covalent bonds at the same time to carry out high-density DNA immobilization and suppression of nucleic acid or protein adsorption. In actuality, first, Anodisc (GE Healthcare Japan Corp.) with a pore size of 0.1 μm was dipped in an ethanol solution for 3 minutes. Then, the membrane was washed twice with 0.1% Tween 20+10 mM Tris (pH 8.0) solution and dried. Then, the membrane was treated with UVO$_3$ for 4 minutes and dipped in an ethanol solution containing 3 mg/mL MPC monomer (e.g., Langmuir 26. 13028-13032 (2010)) as the silanated MPC polymer and 0.3 mg/mL silane coupling agent GTMSi (GTMSi: 3-glycidoxypropyltrimethoxysilane; Shin-Etsu Chemical Co., Ltd.) for 1 hour. After washing with ethanol, heat treatment was carried out at 120° C. for 1 hour in an oven. Next, a PDMS sheet with compartments of 20 μm in diameter was layered on the Anodisc. In order to immobilize the nucleic acid probes (5 and 10) onto the porous membrane (3) within each compartment in the PDMS sheet, 0.05 M borate buffer (pH 8.5) containing the first probe (5) (1 mM), the second probe (10) (5 mM), 1% glycerol, and 0.15 M NaCl was injected at 100 pL to each region in the sheet by the same technique as inkjet printers. Then, epoxy groups on the Anodisc were reacted with the 5'-terminal amino groups of the nucleic acid probes at 25° C. for 2 hours in a moisturizing chamber. Finally, in order to block unreacted functional groups on the Anodisc and remove excessive nucleic acid probes, the membrane was washed for 5 minutes with a sufficient amount of a borate buffer (pH 8.5) containing 10 mM Lys, 0.01% SDS, and 0.15 M NaCl. After removal of this washing solution, the membrane was washed at 60° C. using 30 mM sodium citrate buffer (2×SSC, pH 7.0) containing 0.01% SDS and 0.3 M NaCl to remove excessive DNAs. In this way, the immobilization of the nucleic acid probes and surface treatment were completed.

Next, a method for capturing cells using the genetic analysis system thus constructed will be described. First, approximately 1000 cells were washed with 500 μL of 1×PBS, and then, 50 μL of 1×PBS cooled to 4° C. was added thereto to prepare a cell solution. This cell solution was arranged in an array pattern in each cell retention region of FIG. 1(*a*). Specifically, the cell solution was applied from above toward the bottom of the substrate of the genetic analysis system of this Example in which the PDMS sheet having 1000 cell retention regions of 20 μm in diameter located as shown above was layered on the Anodisc for probe immobilization. As a consequence, each cell was retained in each cell retention region, and the remaining solution was ejected as a waste liquid from the undersurface of the Anodisc. In this way, approximately 80% of the cells were able to be trapped one by one in the respective cell retention regions.

Subsequently, each trapped cell in the substrate was lysed by a routine method using a cell lysis reagent, and the obtained mRNA was trapped by the first probe. Then, a tag sequence-introduced cleaved fragment was obtained through the reaction steps described above. In this Example, SuperScript III (Invitrogen Corp.) was used as reverse transcriptase for synthesizing a complementary strand of the mRNA in the complementary strand synthesis step (II); RNase H (Invitrogen Corp.) was used as an enzyme for removing RNA in the degradation step (III); MspI (New England BioLabs Inc.) was used as a restriction enzyme for cleaving single-strand DNA in the cleaved fragment trapping step (IV); and *E. coli* DNA ligase (New England BioLabs Inc.) was used as DNA ligase for use in the binding step (V). The composition of a cell lysis reagent, a reverse transcription reaction reagent, and an RNase H reagent is shown in Tables 1 to 3. Reaction reagents and reaction methods for the restriction enzyme and the DNA ligase employed the attached buffers and protocols.

TABLE 1

Composition of cell lysis reagent (all reagents from Roche)

| Reagent | Concentration (final concentration) |
|---|---|
| Ready-to-use Lysis buffer | ×1 |
| Protector RNase inhibitor | 1 U |

TABLE 2

Composition of reverse transcription reaction reagent (all reagents from Invitrogen)

| Reagent | Added amount |
|---|---|
| ×5 RT buffer | ×1 |
| 0.1M DTT | 0.02M |
| RNase OUT | 40 U |
| 10 mM dNTP mix | 1.5 mM |

TABLE 3

Composition of RNase H reaction reagent (all reagents from Invitrogen)

| Reagent | Concentration (final concentration) |
|---|---|
| ×5 RT buffer | ×1 |
| MgSO$_4$ | 8.3 mM |
| DTT | 0.2 mM |

Figure 4:
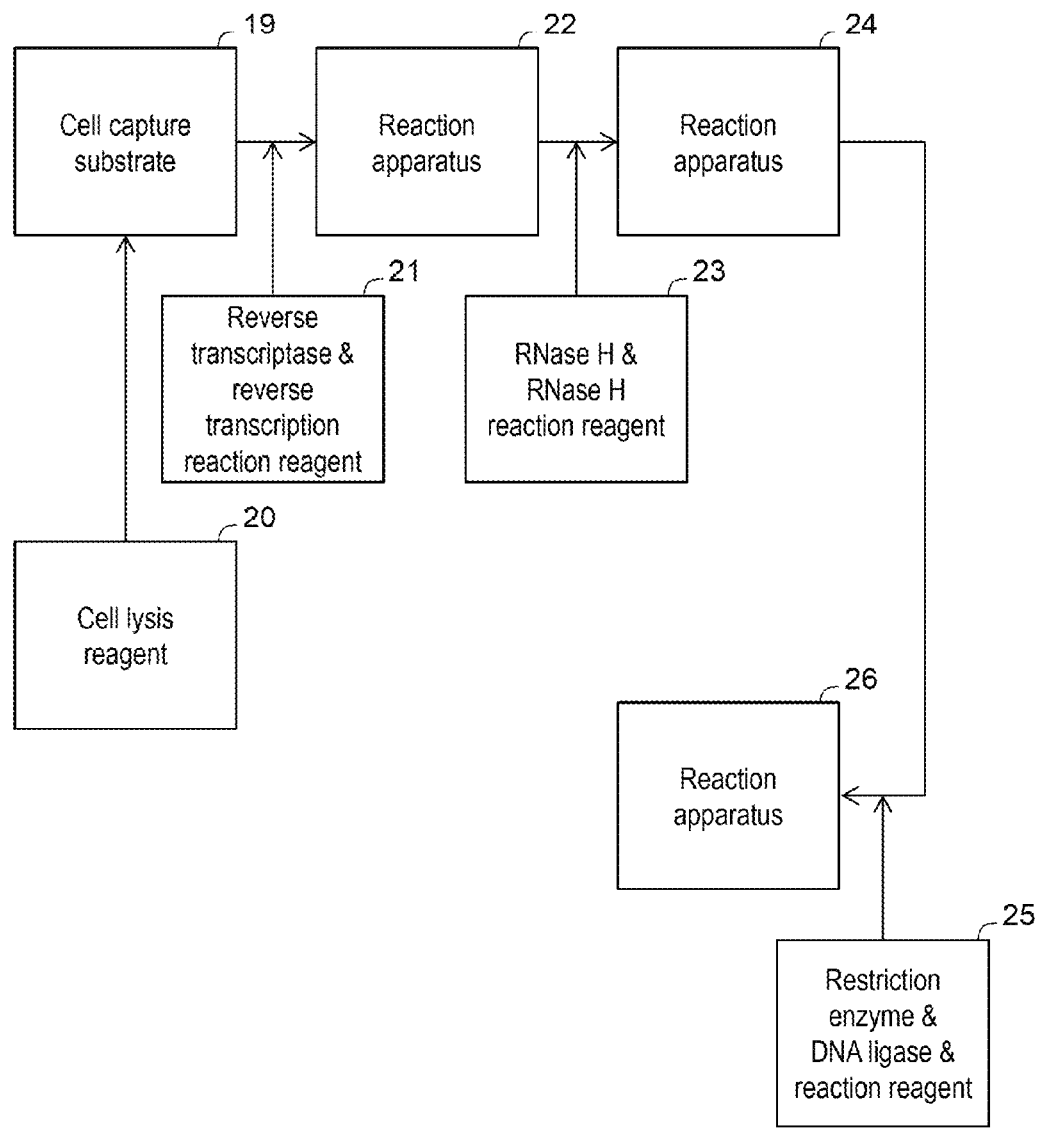
FIG. 4 is a diagram showing one embodiment of the reaction flow of the present invention.

The reaction flow of this Example is shown in FIG. 4. Hereinafter, specific reaction conditions will be described. 4 μL of a cell lysis reagent (20) was added to a cell trapping substrate (19) consisting of the substrate with approximately 1000 cells trapped as described above, and left at room temperature for 5 minutes to lyse the cells. At the same time with the lysis of the cells, the mRNA is trapped by the first probe in the pore present in each cell retention region. Then, a reaction solution (21) consisting of reverse transcriptase (200 U) and a reverse transcription reaction reagent was added thereto, and the mixture was reacted at 50° C. for 50 minutes in a reaction apparatus (22). Then, 1 µL of a reaction solution (23) consisting of RNase H (60 U) and an RNase H reaction reagent was added thereto, and the mixture was reacted at 37° C. for 30 minutes in a reaction apparatus (24). The amount of complementary strands synthesized after the reverse transcription reaction was quantified by qPCR. As a result, it was confirmed that 70% or more complementary strands were able to be synthesized for a house keeping gene GAPDH. Furthermore, 12.5 µL of a reaction solution (25) containing MspI (20 U), *E. coli* DNA ligase (10 U), and a reaction reagent was added thereto, and the mixture was reacted at 37° C. for 1 hour in a reaction apparatus (26). By these reactions, cDNA was synthesized as a complementary strand of the mRNA by using the first probe as a primer, and the obtained cDNA was fragmented while the cleaved fragment was trapped by the second probe and bound thereto with DNA ligase. In this way, the cleaved fragment with the introduced tag sequence specific to each cell retention region was able to be obtained. Finally, nucleic acid amplification reaction was carried out by using the second probe-bound cleaved fragment obtained according to this embodiment as a template and the common sequence as a forward primer, followed by the sequence analysis of the obtained product. Information on the tag sequence contained in the amplification product can be gained to determine the specific gene sequence for each region or region range in the device. All or any two of the degradation step, the cleaved fragment trapping step, and the binding step of this Example may be carried out at the same time.

Example 2

This Example employs a substrate having multiple separated cell retention regions shown in FIG. 1(*b*), and a genetic analysis system in which a first probe and a second probe shown in FIG. 5 are located in each of the cell retention regions, and shows an example where a cleaved fragment of a complementary strand synthesized by using single-strand nucleic acid derived from single-cell as a template, which is trapped by the first probe, is ligated to the second probe with DNA ligase.

The substrate of this construction example is constructed such that each cell retention region retains a single cell. A cell retention region (1) consists of a penetrating-pore with an opening diameter smaller than the diameter of a cell (2) and on the order of 5 to 15 µm in terms of diameter, and a porous membrane (3) at the bottom.

The first probe and the second probe used in this Example, as shown in FIG. 5, are immobilized on carriers, and these carriers with the nucleic acid probes immobilized thereon (nucleic acid probe-immobilized carriers) are located in each cell retention region of the substrate in the construction of FIG. 5(*a*) or 5(*b*). FIG. 5(*a*) shows construction in which a first probe (27) and a second probe (28) are immobilized on the same carrier (29), and this carrier (29) is located in the cell retention region (1). FIG. 5(*b*) shows construction in which the first probe (27) and the second probe (28) are respectively immobilized on different carriers such that the first probe (27) and the second probe (28) are immobilized on a carrier (30) and a carrier (31), respectively. In this construction, both the carriers are mixed and located in the cell retention region (1). The carriers used in this Example were commercially available magnetic beads (Invitrogen Corp.) of 1 µm in diameter coated with streptavidin. The number of nucleic acid probes that can be immobilized per bead is approximately $10^5$. In the case of using, for example, cell retention regions each having a diameter of 30 µm and a depth of 70 µm, approximately $6\times10^4$ beads can be introduced therein, and the total number of nucleic acid probes is approximately $6\times10^9$. Each reaction occurs in the gap between the located beads, and its volume can be estimated to be one several-th of the volume of the cell retention region. Therefore, the density of the nucleic acid probes in the reaction portion is an order of mM. In short, the construction of this Example allows the prepared fragment and the second probe to be reacted very quickly and efficiently and also has a very low probability of losses of cleaved fragments.

FIG. 5(*c*) is a diagram showing the construction of the nucleic acid probes on the carriers shown in FIG. 5(*a*). This diagram shows the sequence construction of the first probe and the second probe. The first probe (27) has the same nucleotide sequence represented by SEQ ID NO: 1 as that of the first probe (5) used in Example 1. The second probe (28) is represented by SEQ ID NO: 3 and differs from the second probe of Example 1 only in the cleaved fragment-complementary sequence (11). The cleaved fragment-complementary sequence (11) in the second probe according to this embodiment consists of a mixed base VN and 3 bases, and these 3 bases consist of "GGW", which is a sequence complementary to a cleaved end after BstNI-mediated cleavage of a recognition sequence "CCWGG" (W=a mixed base of A or T) for a restriction enzyme BstNI capable of cleaving only DNA in an RNA/DNA hybrid strand (Nucleic Acids Research doi 10.1093, 1-12 (2010)). The 5' end of each probe is biotinylated for immobilization on carriers.

In this Example, the second probe (28) may be retained at the bottom of the cell retention region (1). For example, the second probe (28) is embedded in an agarose gel that is dissolved at 80° C., and placed between the cell retention region (1) and the porous membrane (3). The gel is dissolved by heat treatment of 80° C. or higher before the step of producing cleaved fragments so that the second probe can be developed into the cell retention region.

In this Example, the streptavidin-coated magnetic beads (Invitrogen Corp.) of 1 µm in diameter mentioned above were used as the carriers. In the construction of FIG. 5(*a*), the first probe (27) and the second probe (28) were immobilized at approximately $1\times10^{11}$ molecules/$10^7$ beads/µL and approximately $5\times10^{11}$ molecules/$10^7$ beads/µL, respectively, on the carrier (29). In the construction of FIG. 5(*b*), the first probe (27) and the second probe (28) were immobilized at $5\times10^{11}$ molecules/$10^7$ beads/µL on the carriers (30) and (31), respectively, and were mixed with each other so as to exist at a ratio of 1:5. The method for immobilizing the nucleic acid probes onto the carriers followed the manual of the magnetic beads. The carriers with both the nucleic acid probes immobilized thereon and the mixed carriers with the nucleic acid probes respectively immobilized on different carriers were individually injected into an inkjet printer head. The beads on which the tag sequence specific to each cell retention region was immobilized, were individually injected at 6 nL into each cell retention region so that $3\times10^9$ probes were located per cell retention region.

Next, a method for capturing cells using the genetic analysis system of this Example will be described. First, 1000 or less cells were washed with 500 µL of 1×PBS and then suspended in 500 µL of 1×PBS cooled to 4° C. This cell solution was arranged in an array pattern in each region of FIG. 1(*b*). Specifically, Anodisc having a pore size of 0.1 µm was layered with a PDMS sheet of 80 µm in thickness in which 1000 penetrating-pores with an upper diameter of 10 µm and a lower diameter of 50 µm were located. The nucleic acid probe-immobilized carriers were injected into the inside of the cell retention regions formed by the layering of the PDMS sheet and the Anodisc. Unlike the genetic analysis system of Example 1, the Anodisc according to this embodiment plays a role in retaining the carriers. Since the PDMS sheet and the Anodisc are treated to hydrophilization, the solution can be through the penetrating-pores. The cell solution prepared as described above is supplied from above toward the bottom of the substrate so that the cells move by the flow of the solution to retain at the upper portions of the cell retention regions. Since the opening diameter of each cell retention region of this Example is smaller than the diameter of the cell, the cell is trapped in a state immobilized on this region. The trapped cell plays a role as a stopper against the flow of the solution. Therefore, the flow moves, together with untrapped cells, to the upper regions of the cell retention regions that have not yet trapped cells.

Subsequently, each trapped cell in the substrate was lysed by a conventional method using a cell lysis reagent, and the obtained mRNA was trapped by the first probe. Thereafter, a tag sequence-introduced cleaved fragment was obtained. In this Example, steps differ in the order of the degradation step from the steps of Example 1 shown in FIG. 2. Specifically, after synthesis of cDNA, only a DNA strand was cleaved first with a restriction enzyme BstNI capable of cleaving the DNA strand in the obtained RNA/DNA hybrid strand, and then, the RNA was decomposed with RNase H. In this Example, the cleaved fragment is retained in the cell retention region by hybridization with the RNA during the restriction enzyme reaction, and hybridized to the cleaved fragment-complementary sequence (11) of the second probe at the same time with the degradation of the RNA. In this Example, SuperScript III (Invitrogen Corp.) was used as reverse transcriptase for synthesizing a complementary strand of the mRNA in the complementary strand synthesis step (II); RNase H (Invitrogen Corp.) was used as an enzyme for removing RNA, and BstNI (New England BioLabs Inc.) was used as a restriction enzyme for cleaving the RNA/DNA hybrid strand in the degradation step (III); and T4 DNA ligase (New England BioLabs Inc.) was used as DNA ligase for use in the binding step (V). The composition of a cell lysis reagent, a reverse transcription reaction reagent, and an RNase H reagent is the same as that shown in Tables 1 to 3. Reaction reagents and reaction methods for the restriction enzyme and the DNA ligase employed the attached buffers and protocols.

Figure 6:
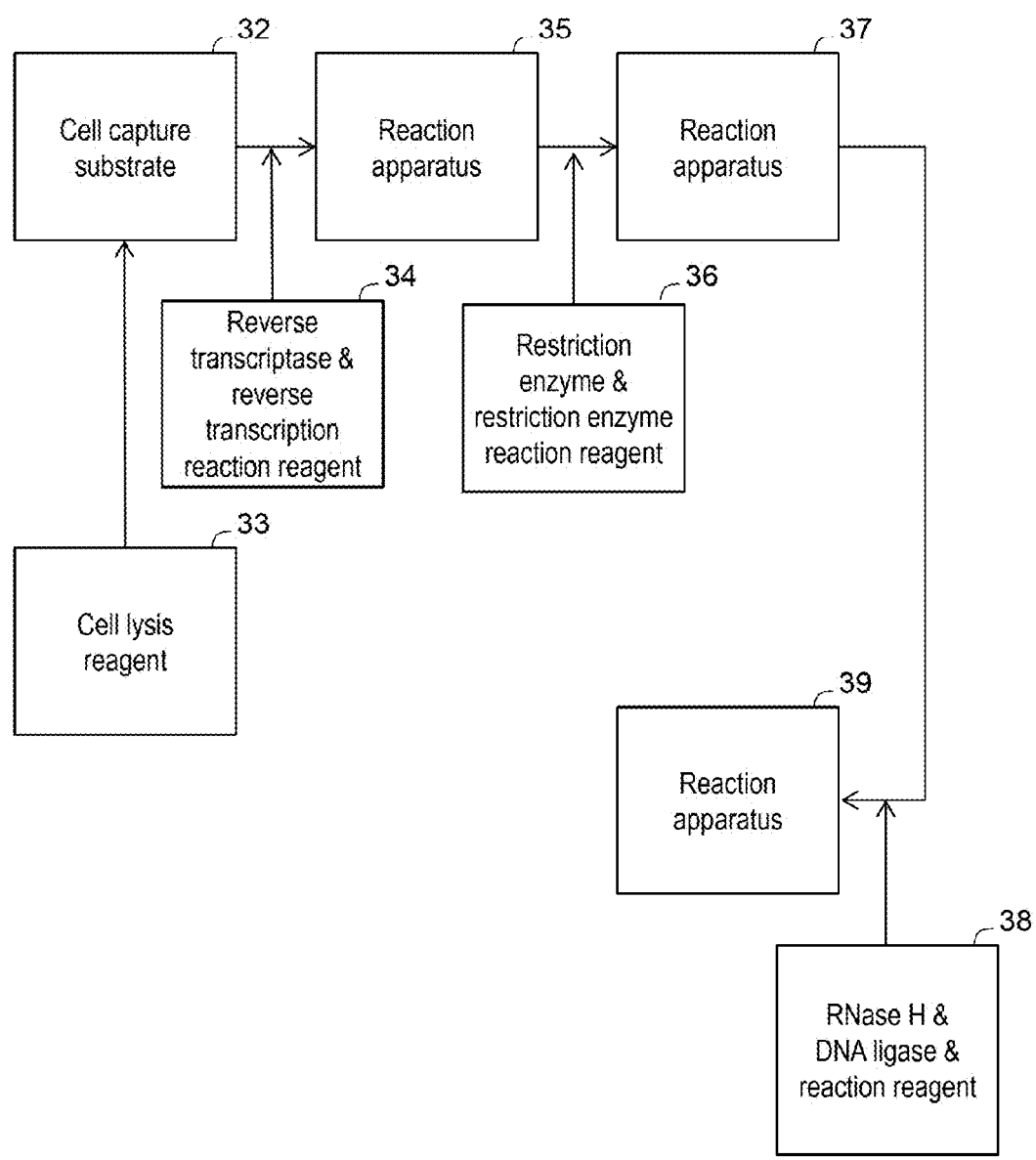
FIG. 6 is a diagram showing one embodiment of the reaction flow of the present invention.

The reaction flow of this Example is shown in FIG. 6. Hereinafter, reaction conditions will be described. 100 µL of a cell lysis reagent (33) was added at a flow rate of 20 µL/min to a cell trapping substrate (32) consisting of the substrate having approximately 1000 cells trapped as described above, and reacted at room temperature for 5 minutes to lyse the cells. At the same time with the cell lysis, the mRNA moves to the cell retention region immediately by flowing the solution, and then the mRNA is trapped by the first probe present in the cell retention region. In this process, the nucleic acid may be allowed to move toward the carrier by applying voltage instead of continuously flowing the cell lysis solution. Then, a reaction solution (34) consisting of reverse transcriptase (200 U) and a reverse transcription reaction reagent was added thereto, and the mixture was reacted at 50° C. for 50 minutes in a reaction apparatus (35). For this reaction, the amount of complementary strands synthesized after the reverse transcription reaction was quantified by qPCR for a house keeping gene GAPDH. As a result, it was confirmed that 80% or more complementary strands were able to be synthesized. Then, 10 µL of a reaction solution (36) containing BstNI (10 U) and a restriction enzyme reaction reagent was added thereto, and the mixture was reacted at 60° C. for 1 hour in a reaction apparatus (37). Next, 5 µL of a reaction solution (38) consisting of RNase H (60 U), DNA ligase (400 U), an RNase H reaction reagent, and a DNA ligase reaction solution was added thereto, and the mixture was reacted at 37° C. for 1 hour in a reaction apparatus (39). By these reactions, cDNA was synthesized as a complementary strand of the mRNA by using the first probe as a primer, and the obtained cDNA was fragmented with BstNI. Then, the cleaved fragment was trapped by the cleaved fragment-complementary sequence of the second probe and ligated thereto with DNA ligase. In this way, the cleaved fragment with the introduced tag sequence specific to each cell retention region was obtained. In this Example, as with Example 1, amplification reaction was carried out by using the second probe-bound cleaved fragment as a template and the common sequence as a Fw primer, followed by the sequence analysis of the synthesized amplification product. On the basis of information on the tag sequence contained therein, the specific gene sequence can be determined for each cell retention region or cell retention region range in the device. All or any two of the cleavage step, the degradation step, and the binding step in the reaction steps of this Example may be carried out at the same time.

Example 3

Figure 7:
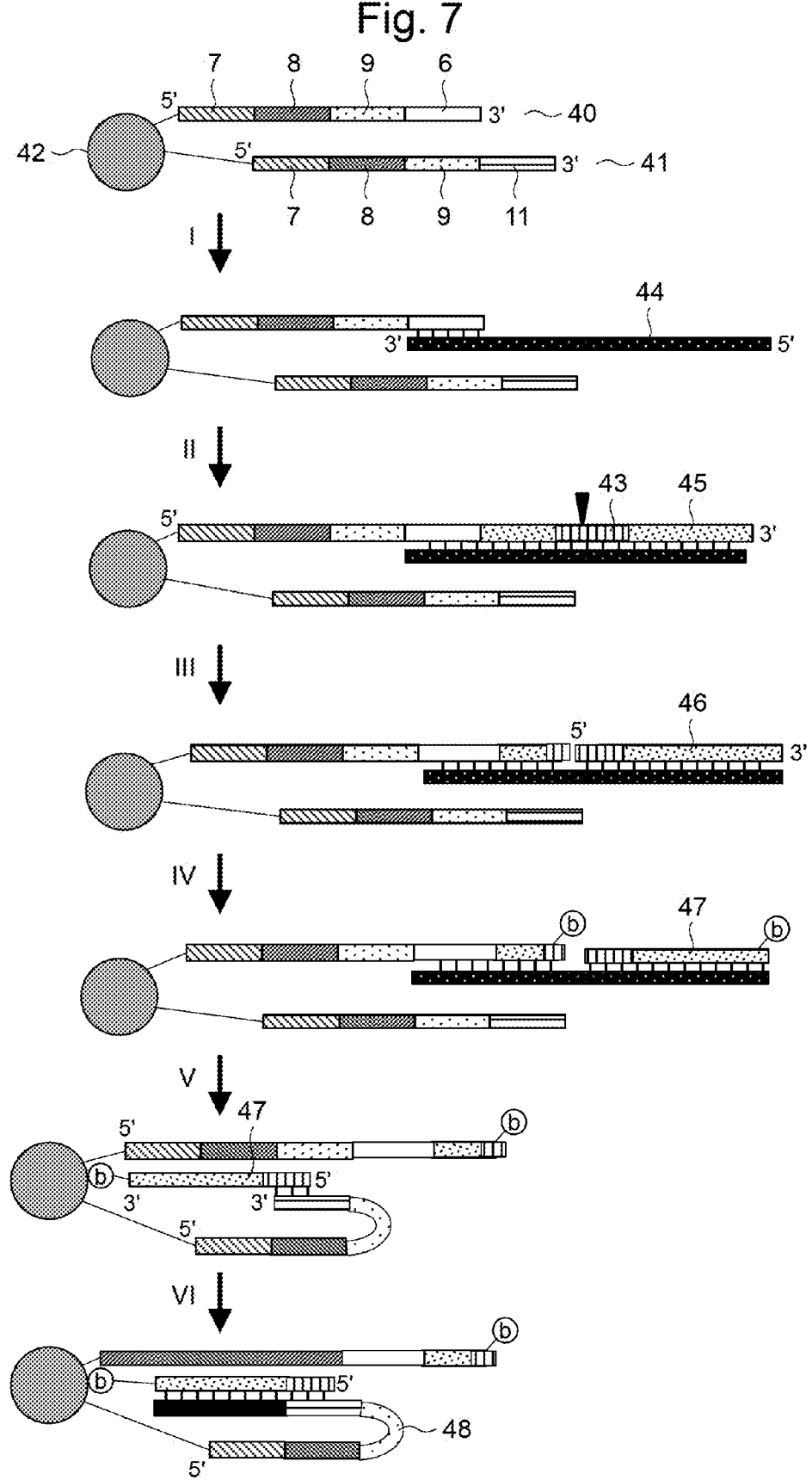
FIG. 7 is a diagram showing one embodiment of nucleic acid probe construction and reaction steps in the genetic analysis system of the present invention.

This Example employs a substrate in which DNA probe-immobilized carriers are introduced in multiple separated cell retention regions shown in FIG. 1(*a*), and a genetic analysis system in which a first probe and a second probe shown in FIG. 7 are located in each of the cell retention regions, and shows a method in which a cleaved fragment of a complementary strand synthesized by using a single cell derived from single-strand nucleic acid, which was trapped by the first probe, as a template is modified and thereby trapped in the cell retention region so that the sequence of the second probe is introduced to a sequence derived from the trapped cleaved fragment.

In this Example, as shown in FIG. 7, a gene analysis system constructed such that a first probe (40) and a second probe (41) were immobilized on the same carrier (42) was used. The sequence of the first probe (40) is represented by SEQ ID NO: 1, and this is the same as in the first and second embodiments. The second probe (41) represented by SEQ ID NO: 4 is constituted by a 30-base common sequence (7), a 5-base tag sequence (8), a nucleic acid amplification correction sequence (9) consisting of a 7-base random sequence, and a 3-base cleaved fragment-complementary sequence with a mixed base VN (11), in this order from the 5' end. In this context, the 3-base cleaved fragment-complementary sequence used consists of "GGW GGW", which is a sequence complementary to a cleaved end after BstNI-mediated cleavage of a recognition sequence (43) "CCWGG" (W=a mixed base of A or T) for a restriction enzyme BstNI capable of cleaving only DNA in an RNA/DNA hybrid strand. The 5' end of each probe is biotinylated for immobilization on carriers. A streptavidin-immobilized carrier was used as the carrier (42) used in this Example. Reaction steps using the genetic analysis system of this Example consist of: a single-strand nucleic acid trapping step (I) of hybridizing mRNA (44), which is the single-strand nucleic acid extracted from the cell, to the trapping sequence (6) of the first probe (40) to trap the mRNA; a complementary strand synthesis step (II) of synthesizing cDNA (45) by using the trapped mRNA (15) as a template and the 3' end of the first probe (40) as a synthesis initiation point; a cleavage step (III) (indicated by arrowhead) of cleaving the cDNA (45) in the mRNA/cDNA hybrid strand with a restriction enzyme BstNI; a modification step (IV) of biotinylating the resulting cleaved fragment (46); a cleaved fragment trapping step (V) of depredating the mRNA and then binding the biotinylated cleaved fragment (47) to streptavidin on the carrier (42) so that a portion of the cleavage sequence in the biotinylated cleaved fragment (47) is hybridized to the cleavage sequence-complementary sequence (11) of the second probe (41) to trap the cleaved fragment; and a second complementary strand synthesis step (VI) of synthesizing second cDNA by using the second probe (41) as a primer and the biotinylated cleaved fragment (47) as a template. In the case of trapping DNA as the nucleic acid of interest in the single-strand nucleic acid trapping step (I) of this Example, the step of depredating the RNA is unnecessary. All or any two of the modification step (IV), the cleaved fragment trapping step (V), and the second complementary strand synthesis step (VI) may be carried out at the same time. Amplification reaction was carried out by using second probe sequence-introduced cDNA (48), which is obtained by the second complementary strand synthesis step as a template and the common sequence (7) as a forward primer, followed by the sequence analysis of the synthesized amplification product. In addition, on the basis of information on the tag sequence contained therein, the specific gene sequence can be determined for each cell retention region or cell retention region range in the device.

Next, construction of a substrate in which DNA probe-immobilized carriers are introduced in multiple separated regions used in this Example is shown in FIG. 8(a), and immobilization patterns of the probes are shown in FIGS. 8(b) and 8(c).

First, as shown in FIG. 8(a), each DNA probe-immobilized carrier (49) was introduced to the inside of the region (1). A cell is trapped in the region, and an extracted nucleic acid is hybridized to the first probe present on the carrier. In this respect, the porous membrane (3) plays a role in retaining the carrier. Next, the immobilization patterns of the probes will be described. As shown in FIG. 8(b), the first probe (40) and the second probe (41) were immobilized on the surface of the same carrier (42). Further, as shown in FIG. 8(c), the first probe (40) and the second probe (41) were immobilized on a carrier (50) and a carrier (51), respectively, and these carriers were mixed with each other to prepare mixed carriers.

In this Example, the same streptavidin-coated magnetic beads (Invitrogen Corp.) of 1 μm in diameter as in Example 2 were used as the carriers. In the construction of FIG. 8(b) or 8(c), the amount of the nucleic acid probes immobilized on the carriers is the same as in Example 2. The nucleic acid probe-immobilized carriers or mixed carriers were individually injected into an inkjet printer head, and the beads on which different sequences were immobilized were individually injected at 6 nL into the cell retention region (1) shown in FIG. 8(a).

Next, a method for trapping cells using the genetic analysis system of this Example will be described. First, 1000 or less cells were washed with 500 μL of 1×PBS without damaging the cells. Then, the solution was removed, and 50 μL of 1×PBS cooled to 4° C. was added to the cells. This cell solution was arranged in an array pattern in each region of FIG. 8(a). Specifically, a PDMS sheet in which 1000 cell retention regions of 20 μm in diameter were located was layered with Anodisc (GE Healthcare Japan Corp.) with a pore size of 0.1 μm. The cell solution is supplied from above toward the bottom of the substrate of the genetic analysis system of this Example so that each cell is retained in each cell retention region. As a result, approximately 80% of the cells were able to be trapped one by one in the respective cell retention regions.

Subsequently, each trapped cell in the substrate was lysed by a routine method using a cell lysis reagent, and the extracted mRNA was trapped by the first probe. Then, a cleaved fragment was biotinylated so that the cleaved fragment was trapped in the cell retention region. Then, the sequence of the second probe was introduced to the sequence of the trapped cleaved fragment. In this Example, as shown in FIG. 7, the cleaved fragment was biotinylated by adding biotin-labeled dUTP to the 3' end using terminal deoxynucleotidyl transferase (hereinafter, referred to as TdT). Then, RNA was decomposed with RNase H while the biotinylated cleaved fragment was trapped by the streptavidin-coated carrier in the cell retention region through a biotin-streptavidin bond. After the trapping, the cleaved fragment was hybridized to the second probe via the cleaved fragment-complementary sequence, and a complementary strand of the cleaved fragment was synthesized with DNA polymerase by using the second probe as a primer. In this Example, SuperScript III (Invitrogen Corp.) was used as reverse transcriptase; RNase H (Invitrogen Corp.) was used as an enzyme for removing RNA; BstNI (New England BioLabs Inc.) capable of cleaving only a DNA strand in an RNA/DNA strand was used as a restriction enzyme; TdT (Thermo Fisher Scientific, Inc.) was used as a biotinylating enzyme; and Platinum Taq Hi Fidelity DNA polymerase (Invitrogen Corp.) was used as DNA polymerase. The composition of a cell lysis reagent, a reverse transcription reaction reagent, and an RNase H reagent is the same as that shown in Tables 1 to 3. The composition of a TdT reaction reagent and a DNA polymerase reaction reagent is shown in Tables 4 and 5. Reaction reagents and reaction methods for the restriction enzyme employed the attached buffers and protocols.

TABLE 4

Composition of TdT reaction reagent (all reagents from Thermo Fisher Scientific)

| Reagent | Added amount |
|---|---|
| ×5 TdT reaction buffer | ×1 |
| 5 uM biotin-11-UTP | 0.5 uM |

TABLE 5

Composition of DNA polymerase reaction reagent (all reagents from Invitrogen)

| Reagent | Added amount |
|---|---|
| ×10 buffer | ×1 |
| 2.5 mM dNTPs | 0.25 mM |
| 50 mM MgSO$_4$ | 2.0 mM |

Figure 9:
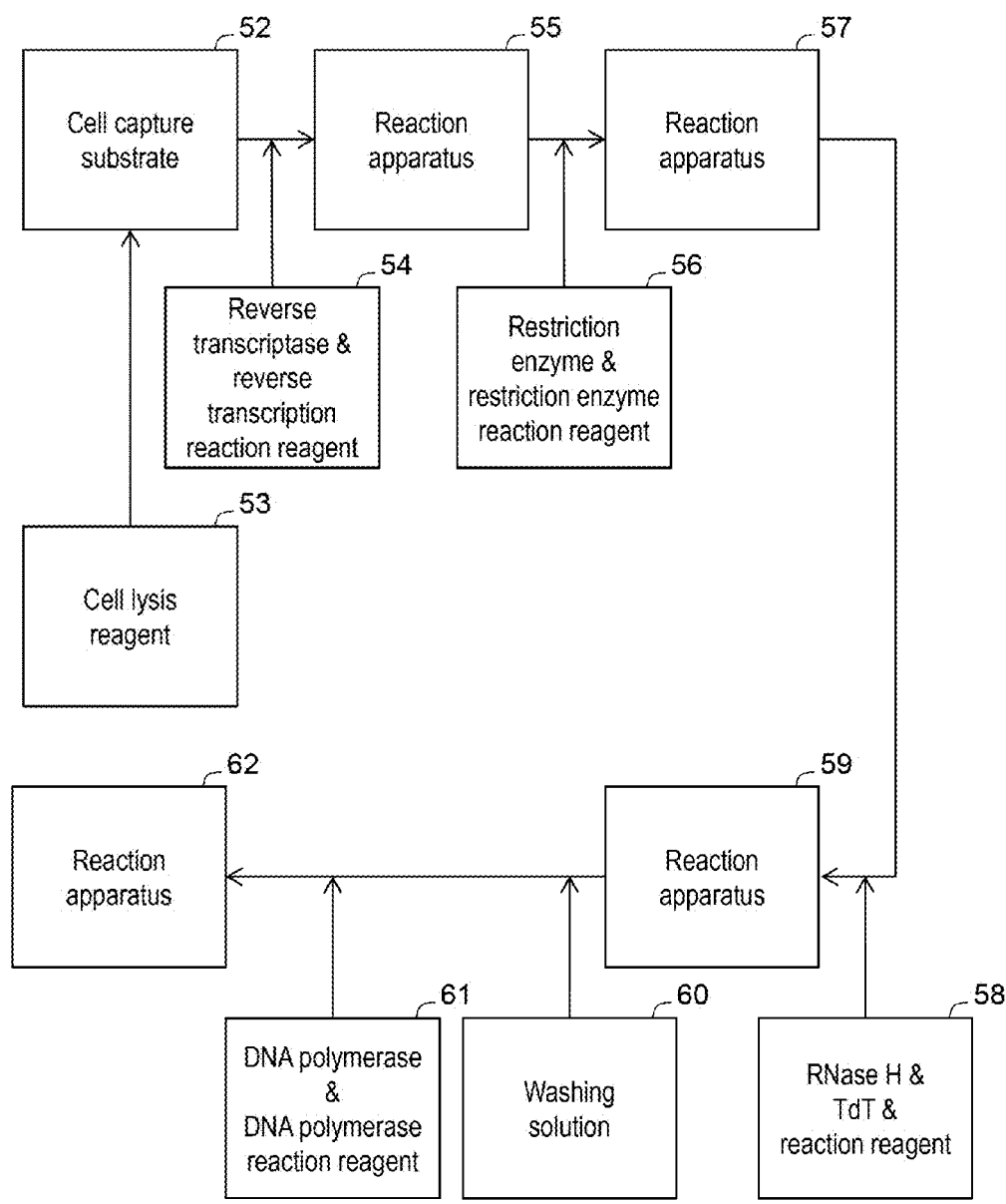
FIG. 9 is a diagram showing one embodiment of the reaction flow of the present invention.

The reaction flow of this Example is shown in FIG. 9. Hereinafter, specific reaction conditions will be described. 2 to 5 μL of a cell lysis reagent (53) was added to a cell trapping substrate (52) consisting of the substrate having approximately 1000 cells trapped as described above, and reacted at room temperature for 5 minutes to lyse the cells. Then, a reaction solution (54) consisting of reverse transcriptase (200 U) and a reverse transcription reaction reagent was added thereto, and the mixture was reacted at 50° C. for 50 minutes in a reaction apparatus (55). Then, 10 µL of a reaction solution (56) containing BstNI (10 U) and a restriction enzyme reaction reagent was added thereto, and the mixture was reacted at 60° C. for 1 hour in a reaction apparatus (57). Next, 11 µL of a reaction solution (58) consisting of RNase H (60 U), TdT (2 U), an RNase H reaction reagent, and a TdT reaction solution reagent was added thereto, and the mixture was reacted at 37° C. for 1 hour in a reaction apparatus (59). The genetic analysis system after the reaction was washed by the addition of 50 µL of a washing solution (60) consisting of 0.1% Tween 20/10 mM Tris (pH 8.0). 10 µL of a reaction solution (61) containing DNA polymerase and a DNA polymerase reaction reagent was added thereto, and the mixture was reacted at 98° C. for 10 seconds, 43° C. for 60 seconds, and 68° C. for 180 seconds in a reaction apparatus (62) to synthesize a complementary strand of a cleaved fragment in the first probe. By these reactions, cDNA was synthesized as a complementary strand of the mRNA by using the first probe as a primer, and the synthesized cDNA was fragmented with BstNI. Then, the cleaved fragment was biotinylated, and a complementary strand of the cleaved fragment was synthesized in the second probe to obtain a sequence derived from the cleaved fragment with the added tag sequence on a cell retention region basis.

Example 4

In this Example, whether a cleaved fragment could be bound to the first probe by a series of reactions consisting of reverse transcription reaction, restriction enzyme reaction, and DNA ligase reaction was tested by quantitative PCR. The immobilization of nucleic acid probes was carried out by the method for immobilization to the carriers in Example 2.

Total RNA was extracted using RNeasy Mini Kit (Qiagen N.V.) from floating cells THP1 of a human monocytic leukemia cell line, and mRNA purified therefrom with Oligotex-dT30 (Takara Bio Inc.) was used as a sample nucleic acid. The extraction and the purification followed the protocols of the reagents. The concentration of the extracted mRNA was measured using nanodrop ND-1000 (Thermo Fisher Scientific, Inc.).

The nucleotide sequences of the first probe and the second probe used in the experiment were the same as in Example 1 (first probe: SEQ ID NO: 1, second probe: SEQ ID NO: 2), and each probe was 5'-terminally biotinylated for use. Magnetic beads (Invitrogen Corp.) of 1 µm in diameter coated with streptavidin were used as carriers. The nucleic acid probes were immobilized on the carriers via the 5'-terminal biotin. In the case of respectively immobilizing the nucleic acid probes onto different carriers (referred to as carriers A), both the probes were immobilized at approximately $5 \times 10^{11}$ molecules/$10^7$ beads/µL on their respective carriers, and the carriers with only the first probe immobilized thereon and the carriers with only the second probe immobilized thereon were mixed with each other at a ratio of 1:5. In the case of immobilizing both the probes on the same carriers (referred to as carriers B), the first probe and the second probe were immobilized at approximately $1 \times 10^{11}$ molecules/$10^7$ beads/µL and approximately $5 \times 10^{11}$ molecules/$10^7$ beads/µL, respectively, on the carriers. The immobilization method followed the manual of the magnetic beads.

FIG. 10 shows a nucleotide sequence (63) (SEQ ID NO: 5) of a binding product of a cleaved fragment derived from GAPDH gene to be amplified and detected by quantitative PCR in this Example, and the second probe. The 1st to 59th bases counted from the 5' end represent the sequence of the second probe, and the 60th to 679th bases represent the sequence of the cleaved fragment derived from the GAPDH gene. A forward primer consisting of the same nucleotide sequence represented by SEQ ID NO: 6 as the common sequence (33) that was shown in the 12th to 32nd bases counted from the 5' end in FIG. 10 and added to the second probe, and a reverse primer consisting of the same nucleotide sequence represented by SEQ ID NO: 7 as a complementary sequence of the 218th to 237th bases were used as a primer set in the quantitative PCR. Also, a detection probe consisting of the same nucleotide sequence represented by SEQ ID NO: 8 as the 206th to 216th bases counted from the 5' end in FIG. 10 was used in the detection of an amplification product. The detection probe is modified 5'-terminally with a FAM dye and 3'-terminally with a non-fluorescent quencher. By use of this primer set, only a product of the cleaved fragment bound with the second probe is amplified, and the amplification product is detected with the detection probe.

In this Example, SuperScript III (Invitrogen Corp.) was used as reverse transcriptase; RNase H (Invitrogen Corp.) was used as an enzyme for removing RNA; MspI (New England BioLabs Inc.) capable of cleaving single-strand DNA was used as a restriction enzyme; and E. coli DNA ligase (New England BioLabs Inc.) was used as DNA ligase. The composition of a reverse transcription reaction reagent and an RNase H reagent is the same as that shown in Tables 2 and 3. Reaction reagents and reaction conditions for the restriction enzyme and the DNA ligase used the attached buffers and protocols.

Figure 11:
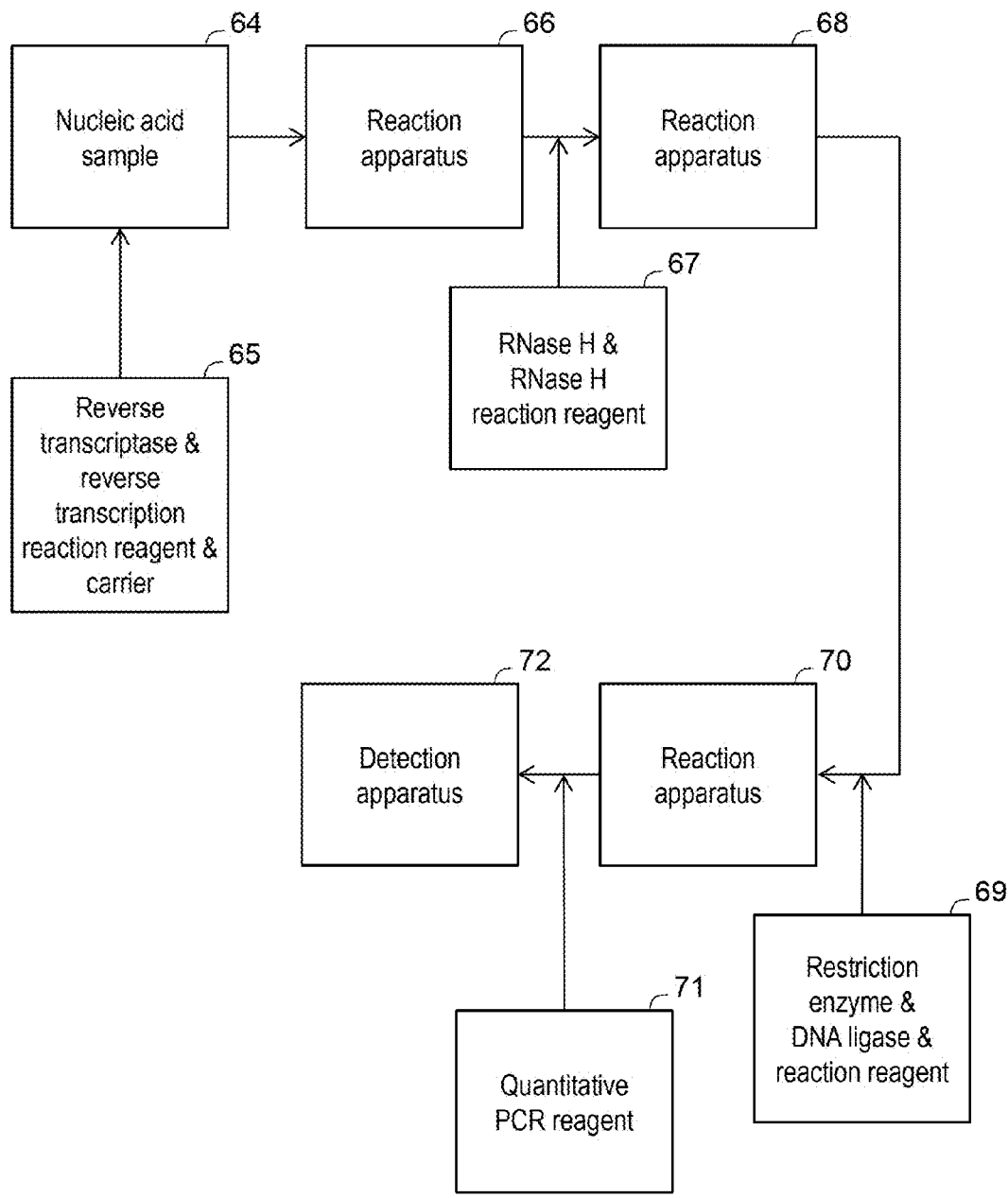
FIG. 11 is a diagram showing one embodiment of the reaction flow of the present invention.

The mRNA and the carriers A and B were used to study the DNA ligase-mediated amount of the binding cleaved-fragment obtained by cleavage after cDNA synthesis to the second probe. The reaction flow is shown in FIG. 11. A reaction solution (65) containing reverse transcriptase (200 U), the carriers A and B (1.5 µL), and a reverse transcription reaction reagent was added to 5 pg of a nucleic acid sample (64) consisting of the mRNA, and the mixture was reacted at 50° C. for 50 minutes in a reaction apparatus (66). Then, 1 µL of a reaction solution (67) containing RNase H (60 U) and an RNase H reaction reagent was added thereto, and the mixture was reacted at 37° C. for 30 minutes in a reaction apparatus (68). Furthermore, 12.5 µL of a reaction solution (69) containing MspI (20 U), E. coli DNA ligase (10 U), and a reaction reagent was added thereto, and the mixture was reacted at 37° C. for 1 hour in a reaction apparatus (70). After the reaction, 19 µL of a quantitative PCR reagent (71) consisting of the forward primer (10 pmol), the reverse primer (10 pmol), the detection probe (2.5 pmol), and Premix Ex Taq (Takara Bio Inc.) was added thereto from which the supernatant was removed. An amplification curve was detected by quantitative PCR in a detection apparatus (72). A sample diluted from a standard curve sample (SEQ ID NO: 9) consisting of a sequence from the 6th to 240th bases counted from the 5' end in FIG. 10 was used as a sample for a standard curve in the quantification. On the basis of the obtained Ct value, the amount of a binding product of the first probe immobilized on the magnetic beads was calculated.

The results are shown in Table 6. The number of GAPDH gene molecules in 5 pg mRNA derived from THP1 cell are approximately $1×10^4$ molecules. In contrast, the amount of the binding product obtained using the carriers A was same as the amount of the GAPDH gene. As for the carriers B, the binding product was obtained at approximately 60% of the number of GAPDH gene molecules. These results demonstrated that a cleaved fragment obtained by the genetic analysis method shown in Example 1 using mRNA as a target nucleic acid can be bound to the second probe.

TABLE 6

The amount of binding cleaved fragment to second probe in first embodiment by using mRNA

| Name of reaction sample | Carrier A | Carrier B |
|---|---|---|
| Binding amount (molecule) to second probe | $1.76 × 10^4$ | $6.48 × 10^3$ |

Example 5

In this Example, whether the genetic analysis method using the genetic analysis system of the present invention would reduce the amount of cleaved fragments moved to other cell retention regions (probability of losses) after cleavage of cDNA with a restriction enzyme, was tested.

The template DNA used in the evaluation to be cleaved with a restriction enzyme has a 100-base sequence and is designed to mimic cDNA synthesized with the first probe. A first probe consisting of the nucleotide sequence represented by SEQ ID NO: 10 is constituted by a sequence with 15 consecutive bases of dTTP, a 4-base restriction enzyme recognition sequence cleavable with restriction enzymes MspI and HpaII, and an 81-base trapping sequence complementary to a portion of GAPDH gene, in this order from the 5' end. The 5' end of the first probe is biotinylated. Different second probes among substrates are used in order to confirm the amount of cleaved fragments moved. Here, two types of second probes are used. Second probe A has the same nucleotide sequence represented by SEQ ID NO: 2 as that used in Example 1, and second probe B consists of the nucleotide sequence represented by SEQ ID NO: 11 and differs from the second probe A only in the sequence specific to each cell retention region. Both the second probes are 5'-terminally biotinylated. A primer set and a detection probe for using in quantitative PCR are as follows: the forward primer consists of the nucleotide sequence represented by SEQ ID NO: 12, which corresponds to the 20th to 32nd bases from the 5' end of the template DNA, and the reverse primer consists of the nucleotide sequence represented by SEQ ID NO: 13, which is a complementary sequence of the 1st to 20th bases from the 3' end of the template DNA. The detection probe consists of the nucleotide sequence represented by SEQ ID NO: 14, which corresponds to the 41st to 58th bases from the 5' end of the template DNA, and is modified 5'-end with a FAM dye and 3'-end with a non-fluorescent quencher. Since a sequence at and subsequent to the 17th base from the 5' end of the template DNA is cleaved by restriction enzyme, the primers 1 and 2 and the detection probe 1 can be used to detect a 3'-side of cleaved fragment obtained after the restriction enzyme.

In the detection of the amount of cleaved fragments moved, the construction of Example 2 is shown in FIGS. 12A and 12B, and control construction free from the second probe for comparison is shown in FIG. 12C. In this Example, substrates with 81 cell retention regions having a pore size of 20 μm were placed in proximity and evaluated for the amount of cleaved fragments moved between the substrates.

In the construction of the present method 1 shown in FIG. 12A, substrate A (74) and substrate B (75) are placed in proximity in a reaction vessel (73). A carrier (78) on which template DNA (76) and second probe A (77) are immobilized at a ratio of 1:1 is injected into the cell retention region of the substrate A (74). On the other hand, a carrier (80) on which second probe B (79) is immobilized is injected into the cell retention region of the substrate B (75).

In the construction of the present method 2 shown in FIG. 12B, the construction of a carrier injected into substrate A (81) in a reaction vessel (73) differs from that of the present method 1. A carrier (82) on which template DNA (76) is immobilized, and a carrier (83) on which second probe A (77) is immobilized are injected in equal amounts into the cell retention region of the substrate A (81). On the other hand, the construction of substrate B (75) is the same as the construction of the present method 1.

The control shown in FIG. 12C is constructed such that the second probe for trapping a cleaved fragment is not located in a substrate. Only a carrier (85) on which template DNA (76) is immobilized is injected into the region of substrate A (84). When cleavage and binding reactions were carried out with a restriction enzyme and DNA ligase in the control construction having no second probe in this cell retention region, and the construction of the present method 1 or 2 with the second probe therein, the amount of cleaved fragments moved from the substrate A to the substrate B was calculated by quantitative PCR.

Next, the immobilization of the probes onto the carriers shown in FIG. 12 will be described. The same streptavidin-coated magnetic beads (Invitrogen Corp.) of 1 μm in diameter as those used in Examples 2 and 3 were used as the carriers. The template DNA or the first probe were immobilized at approximately $3×10^3$ molecules/$10^7$ beads/μL on the carriers. These carriers were injected into cell retention regions on the substrates. The immobilization method followed the manual of the magnetic beads. A PDMS sheet of 80 μm in thickness in which the 81 cell retention regions having a diameter of 20 μm were located, and Anodisc (GE Healthcare Japan Corp.) with penetrating-pores of 0.1 μm in diameter were layered and used as each substrate to which the carriers were introduced.

In this Example, MspI (New England BioLabs Inc.) capable of cleaving single-strand DNA was used as a restriction enzyme; *E. coli* DNA ligase (New England BioLabs Inc.) was used as DNA ligase; and buffers, etc., attached to the restriction enzyme and the DNA ligase were used as reaction reagents.

Figure 13:
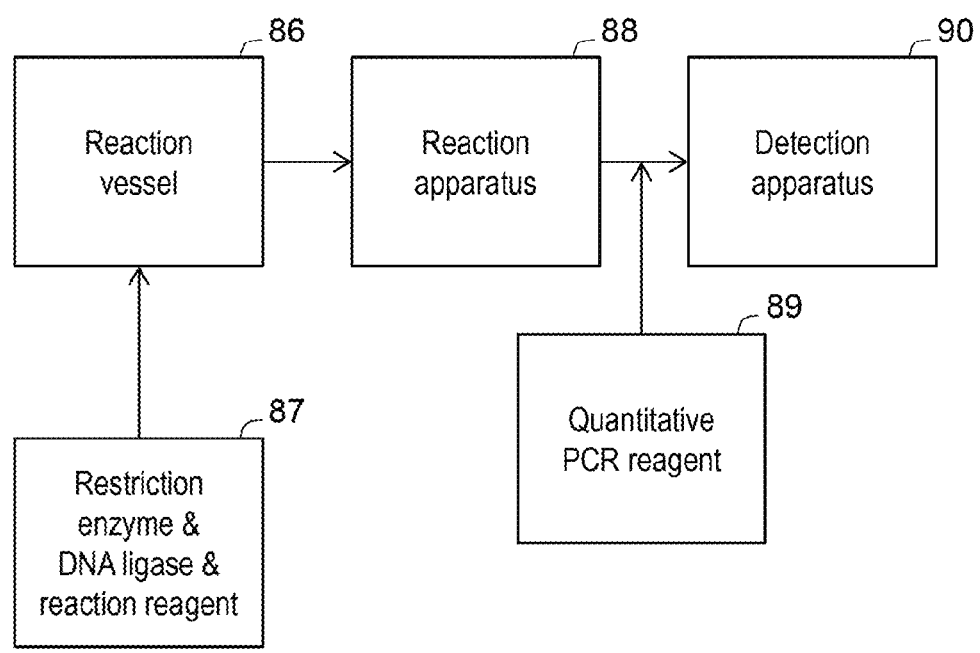
FIG. 13 is a diagram showing one embodiment of the reaction flow of the present invention.

The reaction flow for the present methods 1 and 2 and the control is shown in FIG. 13. 12.5 μL of a reaction solution (87) containing MspI (20 U), *E. coli* DNA ligase (10 U), and a reaction reagent was added to a reaction container (86) consisting of the reaction vessel (73) of FIG. 12A, 12B, or 12C in which each carrier was injected in each substrate, and the mixture was reacted at 37° C. for 1 hour in a reaction apparatus (88). Then, the substrates A and B were collected, and 19 μL of a quantitative PCR reagent (89) consisting of the primer 1 (10 pmol), the primer 2 (10 pmol), the detection probe 1 (2.5 pmol), and Premix Ex Taq (Takara Bio Inc.) was added to each substrate after the reaction. An amplification curve was detected by quantitative PCR in a detection apparatus (90). A sample diluted from a standard curve sample consisting of the nucleotide sequence represented by SEQ ID NO: 15 immobilized on the carrier was used as a sample for a standard curve in the quantification. The standard curve sample has an 84-base sequence and is designed to mimic a sequence on the 3'-terminal side of the cleaved template DNA. The 5' end of the standard curve sample is biotinylated. From a value calculated on the basis of the Ct value obtained from the standard curve, the amounts of detected products obtained in the substrates A and B were calculated. As a result, the total sum of the amounts of detected products was calculated as a value equivalent to the amount of the template DNA (approximately $4.5 \times 10^3$ molecules). Thus, the ratio of the amount of cleaved fragments present in the substrate B was normalized to the total amount of detected products defined as 100%. The results are shown in Table 7. In contrast to 1% or less in the present methods 1 and 2, the ratio was 8.7% in the control construction free from the second probe, indicating approximately 10% of contaminating cleaved fragments. The volume of the region in this Example was $2.5 \times 10^{-8}$ cm$^3$, and the density of the probes was approximately 40 pM, which was lower by approximately $10^{-7}$ as compared with Examples 1 to 4. It was demonstrated that in the construction of the present invention, the movement of cleaved fragments to other regions is very low even at the density of the nucleic acid probes in this Example.

TABLE 7

Amount of fragment moved depending on difference in configuration

| Name of reaction sample | Present method 1 | Present method 2 | Control |
|---|---|---|---|
| Amount of cleaved fragment moved onto substrate B (%) | 0.8 | 0 | 8.7 |

INDUSTRIAL APPLICABILITY

According to the present invention, the sequencing, quantification, and identification of biomolecules can be carried out as to a large number of cultured cells, a large number of immunocytes or (blood) cancer cells, etc. The state of a cell group and the number of its cells present in a living organism can be measured. This also allows for early diagnosis of cancer or the like or measurement of the heterogeneity of iPS cells.

REFERENCE SIGNS LIST

1: Cell retention region
2: Cell
3: Porous membrane
4, 29, 30, 31, 42, 49, 50, 51, 78, 80, 82, 83, and 85: Carrier
5, 27, and 40: First probe
6: Complementary sequence
7: Common sequence
8: Nucleic acid amplification correction sequence
9: Tag sequence
10, 28, 41, 77, and 79: Second probe
11: Cleaved fragment-complementary sequence
12: Arbitrary sequence
13: Complementary sequence of the arbitrary sequence
14 and 43: Cleavage sequence
15 and 44: mRNA
16 and 45: cDNA
17 and 46: Cleaved fragment
18: Second probe-bound cDNA
19, 32, and 52: Cell trapping substrate
20, 33, and 53: Cell lysis reagent
21, 34, and 54: Reverse transcriptase and reverse transcriptase reaction reagent
22, 24, 26, 35, 37, 39, 55, 57, 59, 62, 66, 68, 70, and 88: Reaction apparatus
23 and 67: RNase H and RNase H reaction reagent
25, 69, and 87: Restriction enzyme, DNA ligase, and reaction reagent
36 and 56: Restriction enzyme and restriction enzyme reaction reagent
38: RNase H, DNA ligase, RNase H reaction reagent, and DNA ligase reaction reagent
47: Biotinylated DNA cleaved fragment
48: Second probe sequence-introduced cDNA
58: RNase H, TdT, RNase H reaction reagent, and TdT reaction reagent
60: Washing solution
61: DNA polymerase and DNA polymerase reaction reagent
63: Nucleotide sequence of a binding product of a cleaved fragment and a second probe
64: Nucleic acid sample
65: Reverse transcriptase, reverse transcription reaction reagent, and carrier
71 and 89: Quantitative PCR reagent
72 and 90: Detection apparatus
73 and 86: Reaction vessel
74, 75, 81, and 84: Substrate
76: Template DNA

FREE TEXT OF SEQUENCE LISTING

SEQ ID NO: 1: Description of an artificial sequence: first probe used in Examples 1, 2, 3, and 4 of the present invention
SEQ ID NO: 2: Description of an artificial sequence: second probe used in Examples 1, 4, and 5 of the present invention
SEQ ID NO: 3: Description of an artificial sequence: second probe used in Example 2 of the present invention
SEQ ID NO: 4: Description of an artificial sequence: second probe used in Example 3 of the present invention
SEQ ID NO: 5: Description of an artificial sequence: ligation product used in Example 4 of the present invention
SEQ ID NO: 6: Description of an artificial sequence: forward primer used in Example 4 of the present invention
SEQ ID NO: 7: Description of an artificial sequence: reverse primer used in Example 4 of the present invention
SEQ ID NO: 8: Description of an artificial sequence: probe for the detection of an amplification product used in Example 4 of the present invention
SEQ ID NO: 9: Description of an artificial sequence: standard curve sample for use in the quantification of an amplification product used in Example 4 of the present invention
SEQ ID NO: 10: Description of an artificial sequence: template DNA used in Example 5 of the present invention
SEQ ID NO: 11: Description of an artificial sequence: second probe used in Example 5 of the present invention
SEQ ID NO: 12: Description of an artificial sequence: forward primer used in Example 5 of the present invention
SEQ ID NO: 13: Description of an artificial sequence: reverse primer used in Example 5 of the present invention
SEQ ID NO: 14: Description of an artificial sequence: probe for the detection of an amplification product used in Example 5 of the present invention
SEQ ID NO: 15: Description of an artificial sequence: standard curve sample for use in the quantification of an amplification product used in Example 5 of the present invention All publications, patents, and patent applications cited herein are incorporated herein by reference in their entirety.

```
                            SEQUENCE LISTING

<160> NUMBER OF SEQ ID NOS: 15

<210> SEQ ID NO 1
<211> LENGTH: 62
<212> TYPE: DNA
<213> ORGANISM: Artificial
<220> FEATURE:
<223> OTHER INFORMATION: designed oligonucleotide probe which is used
      for the primer of the complementary DNA synthesis
<220> FEATURE:
<221> NAME/KEY: misc_feature
<222> LOCATION: (36)..(42)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t

<400> SEQUENCE: 1
ccatctcatc cctgcgtgtc tccgactcag agctannnnn nntttttttt tttttttttt       60 vn                                                                     62

<210> SEQ ID NO 2
<211> LENGTH: 59
<212> TYPE: DNA
<213> ORGANISM: Artificial
<220> FEATURE:
<223> OTHER INFORMATION: designed oligonucleotide probe which is used
      for the ligation to the cDNA fragment
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (47)..(53)
<223> OTHER INFORMATION: n is a, c, g, or t

<400> SEQUENCE: 2
vnccgcgacg tccatctcat ccctgcgtgt ctccgactca gagctannnn nnnacgtcg       59

<210> SEQ ID NO 3
<211> LENGTH: 59
<212> TYPE: DNA
<213> ORGANISM: Artificial
<220> FEATURE:
<223> OTHER INFORMATION: designed oligonucleotide probe which is used
      for the ligation to the cDNA fragment
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (47)..(53)
<223> OTHER INFORMATION: n is a, c, g, or t

<400> SEQUENCE: 3
vnccwcgacg tccatctcat ccctgcgtgt ctccgactca gagctannnn nnnacgtcg       59

<210> SEQ ID NO 4
<211> LENGTH: 39
<212> TYPE: DNA
<213> ORGANISM: Artificial
<220> FEATURE:
<223> OTHER INFORMATION: designed oligonucleotide probe which is used
      for the ligation to the cDNA fragment
<220> FEATURE:
```

```
<221> NAME/KEY: misc_feature
<222> LOCATION: (28)..(34)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t

<400> SEQUENCE: 4
cctctctatg ggcagtcggt gaagctannn nnnnwccvn                               39

<210> SEQ ID NO 5
<211> LENGTH: 738
<212> TYPE: DNA
<213> ORGANISM: Artificial
<220> FEATURE:
<223> OTHER INFORMATION: ligated product of GAPDH gene fragment with
      probe
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (47)..(53)
<223> OTHER INFORMATION: n is a, c, g, or t

<400> SEQUENCE: 5
vnccgcgacg tccatctcat ccctgcgtgt ctccgactca gagctannnn nnnacgtcgc        60 ggagggcca tccacagtct tctgggtggc agtgatggca tggactgtgg tcatgagtcc       120
ttccacgata ccaaagttgt catggatgac cttggccagg ggtgctaagc agttggtggt      180
gcaggaggca ttgctgatga tcttgaggct gttgtcatac ttctcatggt tcacacccat      240
gacgaacatg ggggcatcag cagaggggc agagatgatg accctttggg ctcccccctg       300
caaatgagcc ccagccttct ccatggtggt gaagacgcca gtggactcca cgacgtactc      360
agcgccagca tcgccccact tgattttgga gggatctcgc tcctggaaga tggtgatggg      420
atttccattg atgacaagct tcccgttctc agccttgacg gtgccatgga atttgccatg      480
ggtggaatca tattggaaca tgtaaaccat gtagttgagg tcaatgaagg ggtcattgat      540
ggcaacaata tccactttac cagagttaaa agcagccctg gtgaccaggc gcccaatacg      600
accaaatccg ttgactccga ccttcacctt ccccatggtg tctgagcgat gtggctcggc      660
tggcgacgca aaagaagatg cggctgactg tcgaacagga ggagcagaga gcgaagcggg      720
aggctgcggg ctcaattt                                                    738

<210> SEQ ID NO 6
<211> LENGTH: 21
<212> TYPE: DNA
<213> ORGANISM: Artificial
<220> FEATURE:
<223> OTHER INFORMATION: designed oligonucleotide forward primer which
      is used in the amplification of the ligation sample

<400> SEQUENCE: 6
ccatctcatc cctgcgtgtc t                                                 21

<210> SEQ ID NO 7
<211> LENGTH: 21
<212> TYPE: DNA
<213> ORGANISM: Artificial
<220> FEATURE:
<223> OTHER INFORMATION: designed oligonucleotide reverse primer which
      is used in the amplification of the ligation sample
```

```
<400> SEQUENCE: 7
tgggtgtgaa ccatgagaag t                                              21

<210> SEQ ID NO 8
<211> LENGTH: 11
<212> TYPE: DNA
<213> ORGANISM: Artificial
<220> FEATURE:
<223> OTHER INFORMATION: designed oligonucleotide probe which is used
      for the detection of the amplification products

<400> SEQUENCE: 8
aggctgttgt c                                                         11

<210> SEQ ID NO 9
<211> LENGTH: 234
<212> TYPE: DNA
<213> ORGANISM: Artificial
<220> FEATURE:
<223> OTHER INFORMATION: designed oligonucleotide template which is used
      for the reference standard
<220> FEATURE:
<221> NAME/KEY: misc_feature
<222> LOCATION: (41)..(47)
<223> OTHER INFORMATION: n is a, c, g, or t

<400> SEQUENCE: 9
gacgtccatc tcatccctgc gtgtctccga ctcagagcta nnnnnnnacg tcgcggaggg     60
gccatccaca gtcttctggg tggcagtgat ggcatggact gtggtcatga gtccttccac   120
gataccaaag ttgtcatgga tgaccttggc caggggtgct aagcagttgg tggtgcagga   180
ggcattgctg atgatcttga ggctgttgtc atacttctca tggttcacac ccat         234

<210> SEQ ID NO 10
<211> LENGTH: 100
<212> TYPE: DNA
<213> ORGANISM: Artificial
<220> FEATURE:
<223> OTHER INFORMATION: designed oligonucleotide template

<400> SEQUENCE: 10
tttttttttt ttttccggc actgaatctc ccctcctcac agttgccatg tagacccctt     60
gaagagggga ggggcctagg gagccgcacc ttgtcatgta                         100

<210> SEQ ID NO 11
<211> LENGTH: 52
<212> TYPE: DNA
<213> ORGANISM: Artificial
<220> FEATURE:
<223> OTHER INFORMATION: designed oligonucleotide probe which is used
      for the ligation to the cDNA fragment
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (40)..(46)
<223> OTHER INFORMATION: n is a, c, g, or t

<400> SEQUENCE: 11
vnccgcgacg tcctctctat gggcagtcgg tgatagctan nnnnnnacgt cg             52

<210> SEQ ID NO 12
<211> LENGTH: 22
<212> TYPE: DNA
```

```
<213> ORGANISM: Artificial
<220> FEATURE:
<223> OTHER INFORMATION: designed oligonucleotide forward primer which
      is used in the amplification of the reaction sample

<400> SEQUENCE: 12
cactgaatct cccctcctca ca                                              22

<210> SEQ ID NO 13
<211> LENGTH: 20
<212> TYPE: DNA
<213> ORGANISM: Artificial
<220> FEATURE:
<223> OTHER INFORMATION: designed oligonucleotide reverse primer which
      is used in the amplification of the reaction sample

<400> SEQUENCE: 13
tacatgacaa ggtgcggctc                                                 20

<210> SEQ ID NO 14
<211> LENGTH: 17
<212> TYPE: DNA
<213> ORGANISM: Artificial
<220> FEATURE:
<223> OTHER INFORMATION: designed oligonucleotide probe which is used
      for the detection of the amplification sample

<400> SEQUENCE: 14
agttgccatg tagaccc                                                    17

<210> SEQ ID NO 15
<211> LENGTH: 84
<212> TYPE: DNA
<213> ORGANISM: Artificial
<220> FEATURE:
<223> OTHER INFORMATION: designed oligonucleotide template which is used
      for the reference standard

<400> SEQUENCE: 15
cggcactgaa tctcccctcc tcacagttgc catgtagacc ccttgaagag gggaggggcc     60
tagggagccg caccttgtca tgta                                            84
```

The invention claimed is:

1. A genetic analysis system comprising:
   a substrate comprising one or more cell retention region(s) each capable of retaining a single-cell;
   a first probe comprising a capturing sequence that comprises a sequence complementary to a portion of the nucleotide sequence of a single-strand nucleic acid extracted from the cell retained in the cell retention region and traps the extracted single-strand nucleic acid, and a tag sequence specific to each cell retention region, wherein the first probe is located in the cell retention region; and
   a second probe comprising a cleaved fragment-complementary sequence that comprises a sequence complementary to a portion of the nucleotide sequence of a cleaved fragment resulting from the cleavage of a complementary strand synthesized by using the single-strand nucleic acid trapped by the first probe as a template, and forms base pairing with the cleaved fragment, and the tag sequence specific to each cell retention region, wherein the second DNA probe is located in the cell retention region.

2. The genetic analysis system according to claim 1, wherein the first probe and the second probe each further comprise at least one of a common sequence and a nucleic acid amplification correction sequence.

3. The genetic analysis system according to claim 1, wherein the cleaved fragment resulting from the cleavage of a complementary strand synthesized by using the single-strand nucleic acid as a template with a restriction enzyme.

4. The genetic analysis system according to claim 3, wherein the cleaved fragment-complementary sequence comprises a sequence complementary to a cleaved end after the cleavage with the restriction enzyme.

5. The genetic analysis system according to claim 1, wherein
   the second probe further comprises a stem sense strand consisting of an arbitrary nucleotide sequence, and a stem antisense strand consisting of a nucleotide sequence complementary to the stem sense strand, wherein
   any one of the stem sense strand and the stem antisense strand is located at the 3' end of the second probe, and the other strand is located adjacent to the 3'-terminal side of the cleaved fragment-complementary sequence positioned at the 5' end of the second probe, and both the strands are hybridized with each other within the second probe to form a stem structure.

6. The genetic analysis system according to claim 1, wherein at least one of the first probe and the second probe is immobilized on a carrier retained on the surface of the cell retention region.

7. The genetic analysis system according to claim 6, wherein at least one of the first probe and the second probe is immobilized on the carrier via a joint molecule.

8. The genetic analysis system according to claim 6, wherein the first probe and the second probe are immobilized on the same carrier or different carriers.

9. The genetic analysis system according to claim 6, wherein the 5'-terminal portion of at least one of the first probe and the second probe is immobilized on the carrier.

10. The genetic analysis system according to claim 6, wherein a site other than the terminal portion of at least one of the first probe and the second probe is immobilized on the carrier.

11. The genetic analysis system according to claim 1, wherein at least one or more of an existing density of the first probe and an existing density of the second probe per cell retention region is 5 pM or larger.

12. The genetic analysis system according to claim 1, wherein the location of the second probe in the cell retention region is dissociable depending on change in environment.

13. The genetic analysis system according to claim 12, wherein the environment is temperature or light.

14. A genetic analysis method comprising:
a first step of supplying multiple cells onto a substrate of a genetic analysis system according to claim 1 so that the cells are retained one by one in respective cell retention regions;
a second step of extracting a nucleic acid from each cell retained in the cell retention region in the first step, and capturing the single-strand nucleic acid by a first probe in the cell retention region;
a third step of using the first probe as a primer and the single-strand nucleic acid trapped in the second step as a template to synthesize a complementary strand thereof;
a fourth step of fragmenting the complementary strand synthesized in the third step, and capturing the cleaved fragment in the same cell retention region thereas; and
a fifth step of introducing a tag sequence to the trapped cleaved fragment on a cell retention region basis.

15. The genetic analysis method according to claim 14, wherein the trapping of the cleaved fragment in the cell retention region in the fourth step is carried out via hybridization to the cleaved fragment-complementary sequence of the second probe.

* * * * *